United States Patent [19]
Noren et al.

[11] Patent Number: 5,691,140
[45] Date of Patent: Nov. 25, 1997

[54] BIDIRECTIONAL IN VITRO TRANSCRIPTION VECTORS UTILIZING A SINGLE RNA POLYMERASE FOR BOTH DIRECTIONS

[75] Inventors: Christopher J. Noren, Rockport, Mass.; Paul D. Evans, Camp Verde, Ariz.

[73] Assignee: New England Biolabs, Inc., Beverly, Mass.

[21] Appl. No.: 443,640

[22] Filed: May 18, 1995

[51] Int. Cl.$^6$ .............. C12Q 1/68; C12N 15/64; C12N 15/66; C12N 15/70
[52] U.S. Cl. .............. 435/6; 435/172.3; 435/320.1
[58] Field of Search .............. 435/6, 172.3, 320.1

[56] References Cited

PUBLICATIONS

Vieira and Messing, Gene, 19:259–268 (1982).
Vieira and Messing, Methods in Enzymology, 153:3–11 (1987).
Vieira and Messing, Gene, 100:189–194 (1991).
McInnes and Symons, Nucleic Acid Probes, CRC Press, pp. 18–23.
Melton, et al., Nucleic Acids Research, 12:7035–7056 (1984).
Chapman and Burgess, Nucleic Acids Research, 15:5413–5432 (1987).
Chapman, et al., Nucleic Acids Research, 16:4511–4524 (1988).
Schneider and Stormo, Nucleic Acids Research 17:659–674 (1989).
Ikeda, et al., Biochemistry, 31:9073–9080 (1992).
Ikeda, et al., Nucleic Acids Research, 20:2517–2524 (1992).
McAllister, Cell. Mol. Bio. Res., 39:385–391 (1993).
Chamberlain and Ryan, The Enzymes, 15:87–108 (1982).
Strothkamp, et al., Biochemistry, 19:1074–1080 (1980).
Yanisch–Perron, et al., Gene, 33:103–119 (1985).
Kalnins, et al., EMBO J., 2:593–597 (1983).
Christie, et al., Proc. Natl. Acad. Sci. USA, 78:4180–4184 (1981).
Karlovsky & Prell, Nucleic Acids Research, 15:6753 (1987).
Zagursky & Berman, Gene, 27:183–191 (1984).
Riggs, Current Protocols In Molecular Biology, NY:Greene Publishing and J. Wiley & Sons, pp. 16.6.1–16.6.14 (1992).
Slatko, Current Protocols in Molecular Biology, NY:Greene Publishing and J. Wiley & Sons, pp. 7.2.1–7.2.20 (1992).
Moreira and Noren, Biotechniques, 19: 56–59 (1995).
Schenborn and Mierendorf, Nucleic Acids Research, 13:6223–6235 (1985).
Feinberg and Vogelstein, Anal. Biochem., 132:6–13 (1983).
Noren et al. (1995), Miami Bio/Technology Short Reports, vol. 6, p. 74.
Chen et al. (1994), Nucl. Acids Res. 22(11):2114–2120.

*Primary Examiner*—Nancy Degen
*Attorney, Agent, or Firm*—Gregory D. Williams

[57] ABSTRACT

Multipurpose cloning in vitro phagemid vectors are disclosed, which vectors may be used to generate high specific-activity RNA probes. The multipurpose vectors also possess a bidirectional in vitro transcription system. Methods for constructing this system are also disclosed.

15 Claims, 11 Drawing Sheets

BIDIRECTIONAL IN VITRO TRANSCRIPTION VECTORS UTILIZING A SINGLE RNA POLYMERASE FOR BOTH DIRECTIONS

BACKGROUND OF THE INVENTION

This invention relates to a set of multipurpose cloning/in vitro transcription phagemid vectors. These vectors may be used to generate high specific activity RNA probes. These vectors also possess a novel system for bidirectional in vitro transcription. The present invention also relates to methods for constructing and using such bidirectional vectors.

In the 13 years since the development of the pBR322-derived cloning vectors pUC8 and pUC9 (J. Vieira and J. Messing, *Gene*, 19:259–268 (1982)), the first small, high copy number plasmids to incorporate multiple restriction sites in a "polylinker" in the α-complementation locus for lacZ, numerous modifications have been made to these useful and popular vectors. For example, i) filamentous phage replication origins have been added to facilitate isolation of single-stranded vector DNA for sequencing or in vitro mutagenesis (J. Vieira and J. Messing, *Methods in Enzymology*, 153:3–11 (1987)); ii) phage promoters for in vitro transcription of RNA probes from cloned inserts have been installed (J. L. McInnes and R. J. Symons, *Nucleic Acid Probes*, Boca Raton: CRC Press, pp. 18–23 (1989)); and iii) different selectable markers have been exchanged with the ampicillin resistance gene (J. Vieira and J. Messing, *Gene*, 100:189–194 (1991)). Most of these modifications have been simple "plug-ins" to the basic pUC backbone, and maximum flexibility has often been compromised for expedient construction.

At the same time, the addition of new polylinker restriction sites has been unable to keep pace with the discovery and commercial availability of new restriction enzymes. Many recently available enzymes have nondegenerate 6-bp recognition sites and leave 4-base "sticky ends" after cleavage—the features most useful for cloning—but sites for the majority of these enzymes have yet to be included in most cloning vector polylinkers. Accordingly, it would be desirable to have one or more cloning vectors that include these unused sites in polylinkers that are rationally designed from scratch to expand the possible strategies for subcloning or sequencing a cloned DNA fragment. In addition, it would be desirable to streamline the backbone of the vector, i.e. deleting nonessential regions while retaining useful features such as a filamentous phage origin.

The use of RNA probes as an alternative to DNA probes in Southern blotting is rapidly gaining favor, as a result of the greater thermodynamic stability of RNA:DNA hybrids relative to DNA:DNA hybrids (D. Melton, et al., *Nucleic Acids Res.* 12:7035–7056 (1984)). Hybridization of RNA probes to single-stranded DNA targets (or RNA targets in Northern blotting) requires the ability to generate transcripts from either strand of a cloned insert. This is typically achieved with a pair of opposing phage RNA polymerase promoters flanking the vector polylinker (McInnes and Symons, supra), each recognized by a different polymerase (e.g., T7 and T3 promoters). The direction of transcription is determined by which RNA polymerase is used. The disadvantage of a two-polymerase system is that bacteriophage RNA polymerases have different optimum reaction conditions, thereby necessitating working out reaction conditions separately for each direction of transcription. This problem could be bypassed if a single RNA polymerase could be used to transcribe either strand of a cloned DNA insert.

SUMMARY OF THE INVENTION

In accordance with the present invention there is provided a set of multipurpose cloning vectors (hereinafter sometimes also referred to as "LITMUS vectors"). In certain preferred embodiments, the vectors feature the high-copy pUC origin and an M13 origin for single-stranded DNA production, as well as polylinker sites for most commercially available restriction enzymes that recognize nondegenerate hexanucleotide sites and yield 4-base sticky ends upon cleavage. Sites are preferably arranged, without overlaps, to permit linker addition to blunt-ended fragments and unidirectional nested deletions, and are preferably within a marker gene such as the lacZ gene to facilitate blue-white screening.

In accordance with a second embodiment, the polylinkers are flanked by a pair of opposing modified RNA polymerase promoters such as T7 promoters to allow in vitro transcription of either strand of a cloned insert with a single polymerase, e.g., T7 RNA polymerase. Both promoters are recognized, and transcription is initiated, by a single species of RNA polymerase. Selective unidirectional transcription from one promoter may be achieved by cleaving the other at an internally or proximate engineered restriction site. That is, each promoter or neighboring region has a unique predetermined restriction site which when exposed to the corresponding restriction endonuclease renders that promoter inactive. Both modified promoters are fully active under standard RNA probe synthesis conditions.

Finally, the present invention provides methods for engineering predetermined restriction sites into the promoter region of RNA polymerases.

3

Figure 7:
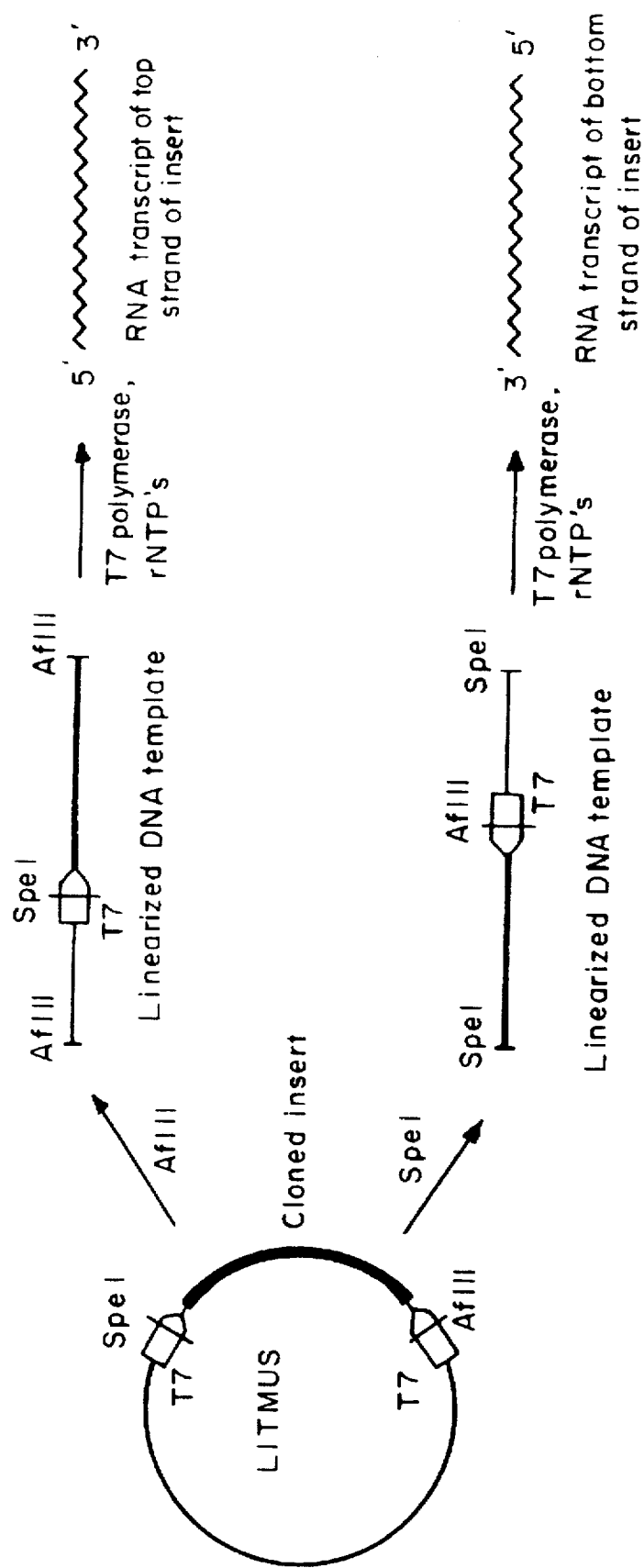

FIG. 7 shows the selective unidirectional transcription of inserts cloned in LITMUS vectors. Specific transcription from the SpeI-site containing T7 promoter is achieved by linearizing with AflIII prior to transcription (top). Transcription from the AflIII promoter is achieved by linearizing with SpeI prior to transcription (bottom). If the cloned insert contains either site, each promoter can alternatively be inactivated by digesting at the polylinker site immediately downstream from that promoter.

Figure 8:
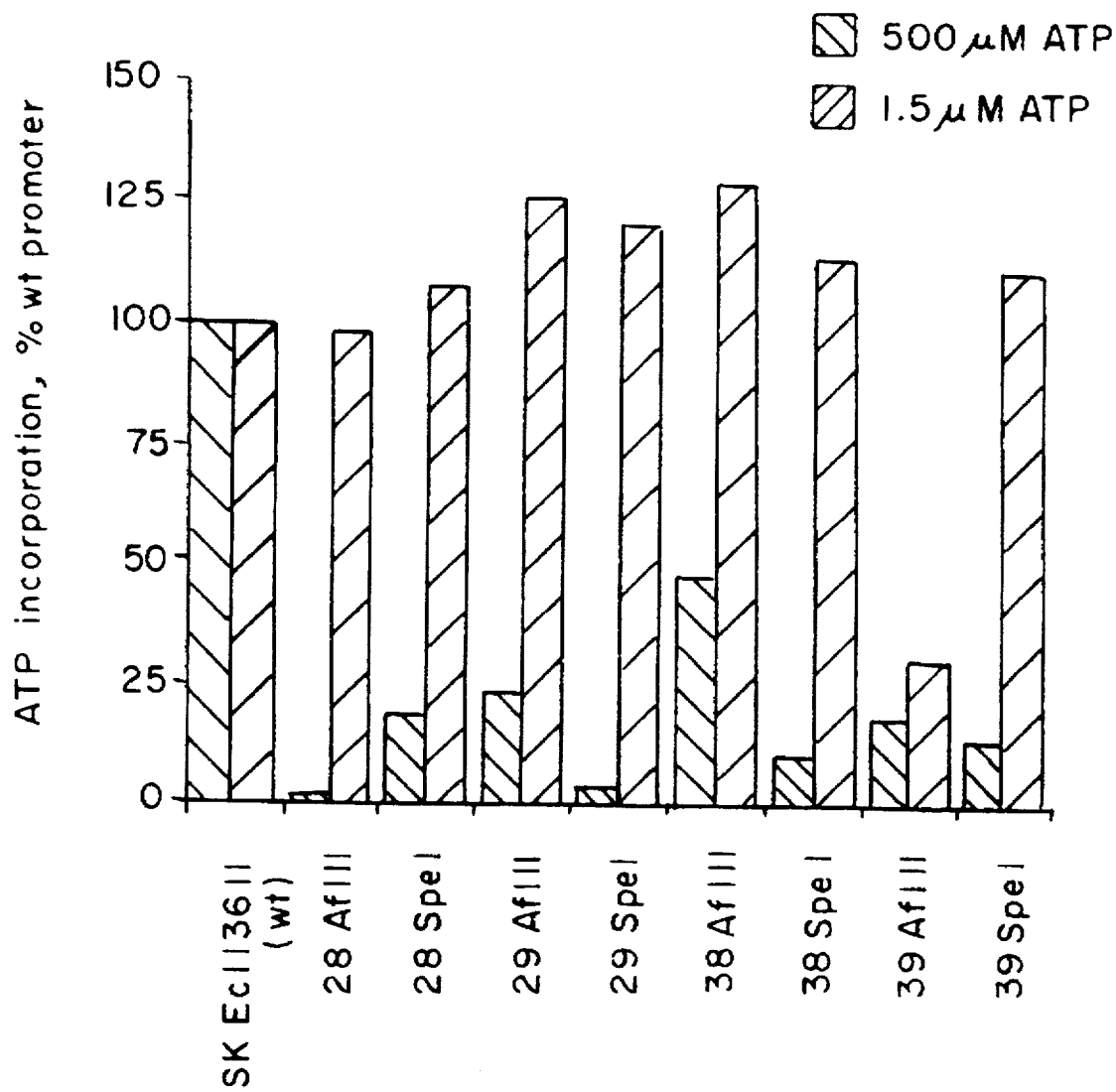

FIG. 8 shows the effect of nucleotide concentration on LITMUS transcription efficiency. Plasmids were digested with the indicated enzymes to yield transcripts of approximately equal length (~120 bases). 10 μl transcription reactions were carried out as described below, using either 500 μM ATP (gray bars) or 1.5 μM ATP (striped bars). Reactions were incubated at 37° C. for 60 min., spotted onto Whatman 3 MM paper disks, washed in 10% trichoroacetic acid, and counted. Each set was normalized to the ATP incorporated from the wild-type T7 promoter in Ecl136II-digested Bluescript SK(−), which was defined as 100%.

Figure 9:
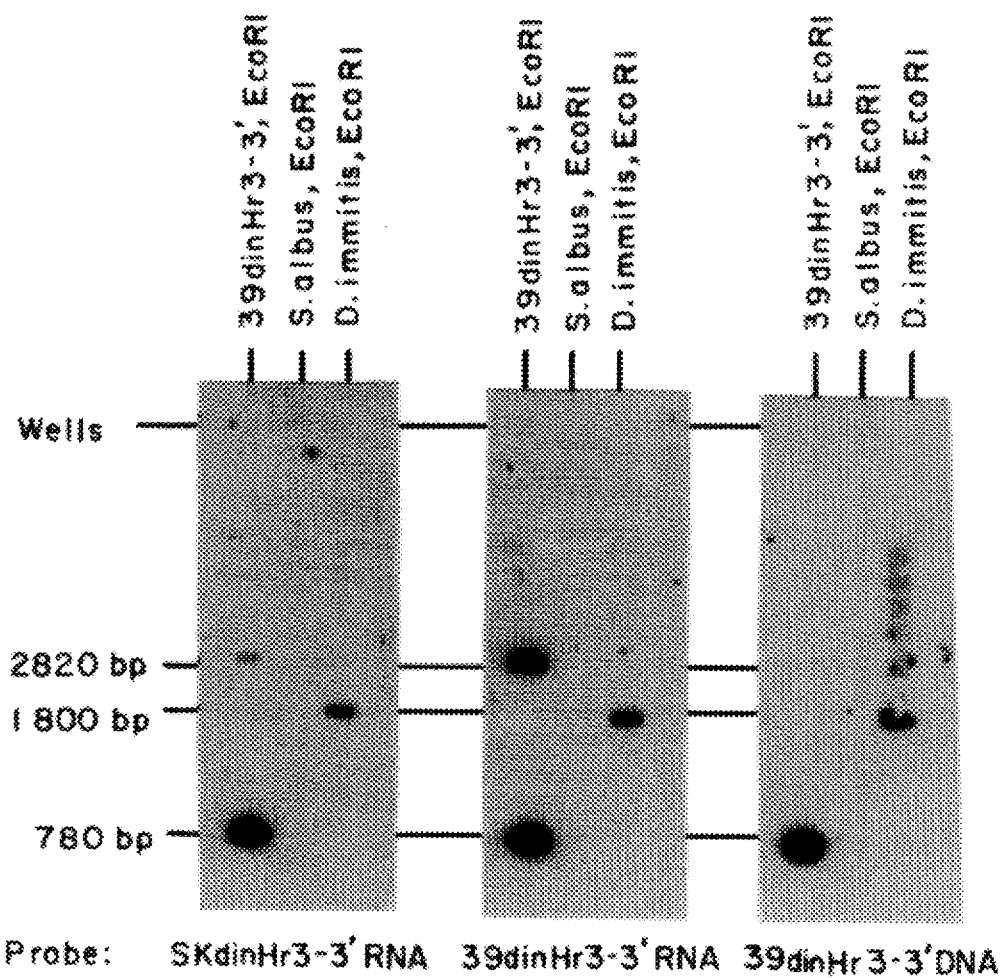

FIG. 9 shows Southern blotting with LITMUS RNA probes. Samples were electrophoresed in triplicate, and blotted and probed with the indicated RNA or DNA probes as described below. Lane 1:1 ng EcoRI-digested LITMUS 39 containing the 780-bp *D. immitis* dinhr3-3' insert (39dinHR3-3'). Lane 2: 1 μg EcoRI-digested *Streptococcus albus* genomic DNA. Lane 3: 3 μg EcoRI-digested *Dirofilaria immitis* genomic DNA. Hybridization of both RNA probes to the 2820-bp LITMUS vector backbone is due to the presence of polylinker sequence in the RNA probe.

DETAILED DESCRIPTION OF THE INVENTION

The present invention relates to multipurpose cloning vectors for use in cloning and/or in vitro transcription. The vectors of the present invention preferably possess a streamlined pUC-derived plasmid backbone, as well as a plethora of unique, conveniently arranged restriction sites. In addition, the vectors of the present invention preferably include a selection system such as the blue/white lacZ α-complementation assay.

The present invention also relates to a unique system in which the aforementioned vector polylinkers are flanked by a pair of modified RNA polymerase promoters such as the T7 promoter, each with a restriction site engineered into the consensus promoter sequence such that cleavage by the corresponding endonuclease inactivates that promoter. The direction of transcription is thus determined by which enzyme is used to linearize DNA template prior to transcription (FIG. 7), so a single set of reaction conditions can be used for both directions. Construction of a vector system employing this concept necessitated determining which restriction sites can be tolerated within the consensus promoter sequence without adversely affecting in vitro transcription efficiency. Accordingly, the present invention also relates to the methods used to construct this unique system. Introduction Of Restriction Sites Into The Consensus T7 Promoter Sequence The vector pDEFEND1 is a pUG18 derivative in which the lacZα sequence has been modified to include opposing T7 and SP6 RNA polymerase promoters flanking the polylinker region (Example I, FIG. 1). Additionally, the backbone of the vector is modified to include the origin of replication from the single-stranded filamentous bacteriophage M13, in order to permit isolation of single-stranded plasmid DNA for in vitro oligonucleotide-directed mutagenesis. This vector was used to test the effects of mutations that introduce restriction sites just prior to the transcription initiation site (+1) of the T7 late promoter sequence $^{-17}$TAATACGACTCACTATAG$^{+1}$ (SEQ ID NO:5). Restriction sites were introduced between positions −1 and −7 (Table I), as a number of groups have demonstrated that single-base changes in this region result in <50% reduction in promoter strength under polymerase-limiting conditions in vitro and in vivo (e.g., K. Chapman and R. Burgess, *Nucleic Acids Res.* 15:5413–5432 (1987), K. Chapman, et al., *Nucleic Acids Res.* 16:4511–4524 (1988), T. Schneider and G. Stormo, *Nucleic Acids Res.* 17:659–674 (1989), R. Ikeda, et al., *Biochemistry* 31:9073–9080 (1992), R. Ikeda, et al., *Nucleic Acids Res.* 20:2517–2524 (1992)), the disclosures of which are hereby incorporated by reference herein. It has been postulated that the T7 promoter is comprised of slightly overlapping domains: the region from −17 to −5 is involved in polymerase-promoter recognition, while the region from −6 to +1 is involved in transcription initiation (i.e., open complex formation) (Chapman *Nucleic Acids Res.* 16:4511–4524 (1988), the disclosure of which is hereby incorporated by reference herein). Cleavage of the promoter within this region would be expected to destroy the promoter, since the actual point of initiation (+1) has been removed. The wild-type promoter already contains a palindromic hexanucleotide sequence, CTATAG, in this region. Unfortunately, there are no available restriction enzymes that uniquely recognize this sequence. In order to confirm that cleavage within the T7 promoter is sufficient to abolish in vitro transcription, wild-type pDEFEND1 was digested with SfcI, which cleaves the degenerate sequence C↓TRYAG (R=A or G, Y=T or C). As expected, no radiolabel incorporation above background was observed when SfcI-linearized pDEFEND1 was used as a template for in vitro transcription. This palindrome was used as a starting point for engineering recognition sites for non-degenerate enzymes. By altering 2 or 4 bases within (or adjacent to) this sequence, a total of eight unique palindromic restriction sites were introduced into the T7 promoter (Table I). The mutations required for introduction of 7 of the sites are at positions which had previously been determined to be tolerant of base substitutions (i.e., the mutant promoters displayed >30% wild-type activity under polymerase-limiting conditions in vitro), although none of the published work involved mutagenesis at more than one position at a time. Introduction of the EcoNI site was expected to provide a negative control for restriction site sequence tolerance, since the required mutation involved reversing a dinucleotide ($T_{-8}C_{-7}$) that has been shown to be critical for promoter function (Chapman (1987) supra). Since the T7 promoter is closely related to promoters for other bacteriophage-encoded RNA polymerases (e.g., T3, SP6, K11, BA14), especially within the initiation region, the analogous positions in these other promoters also provide initial targets for assaying the tolerance of those promoters to introduced restriction sites (W. T. McAllister, *Cell. Mol. Biol. Res.* 39:385–391 (1993), the disclosure of which is hereby incorporated by reference herein).

An alternative strategy for promoter inactivation is to incorporate a Type IIS restiction site downstream from the promoter, oriented such that the corresponding enzyme cleaves within the promoter. Type IIS restriction enzymes are a class of enzymes that recognize non-palindromic DNA sequences and cleave a defined number of bases on one side of the recognition sequence. This strategy has the advantage that modification of the internal sequence of the promoter is unneccessary. The vector pDEFEND1 has a unique site for the Type IIS enzyme BsaI just downstream from the 77 promoter, oriented for cleavage directly at the transcription initiation site. As with SfcI, cleavage of pDEFEND1 with BsaI completely abolished in vitro transcription.

which has probably evolved to carry out open-complex formation by utilizing the binding energy of specific side chain-nucleotide contacts.

In order to confirm that transcription is abolished when each mutant promoter is cleaved at its internal site, all 8

TABLE I

| Template | | ATP incorporated, nM/min | | $K_M$ (linear) | $k_{cat}$ (linear) |
|---|---|---|---|---|---|
| | | Supercoiled | Linearized | | |
| TAATACGACTCACTATAGGG (SEQ ID NO: 6) | | 6420 ± 210 | 898 ± 56 | 5.7 nM | 15 min$^{-1}$ |
| AflII | CTTAAG (SEQ ID NO: 7) | 7790 ± 170 | 392 ± 24 | 13.2 nM | 14 min$^{-1}$ |
| XhoI | CTCGAG (SEQ ID NO: 8) | 5490 ± 60 | 119 ± 4 | | |
| MunI | CAATTG (SEQ ID NO: 9) | 6820 ± 30 | 138 ± 3 | | |
| NcoI | CCATGG (SEQ ID NO: 10) | 7310 ± 170 | 104 ± 7 | | |
| NdeI | CATATG (SEQ ID NO: 11) | 7540 ± 240 | 84 ± 14 | | |
| XbaI | TCTAGA (SEQ ID NO: 12) | 6920 ± 120 | 38 ± 6 | | |
| SpeI | ACTAGT (SEQ ID NO: 13) | 7910 ± 140 | 315 ± 34 | 15.5 nM | 10 min$^{-1}$ |
| EcoNI | CCTACTATAGG (SEQ ID NO: 14) | 760 ± 50 | 10 ± 6 | | |

Transcription of mutant promoters. Templates were supercoiled or linearized with HindIII (91-base transcript) as indicated. Underlined bases denote deviations from wild-type promoter sequence.

Effect Of Introduced Mutations On Supercoiled vs. Linear Template

Figure 2A:
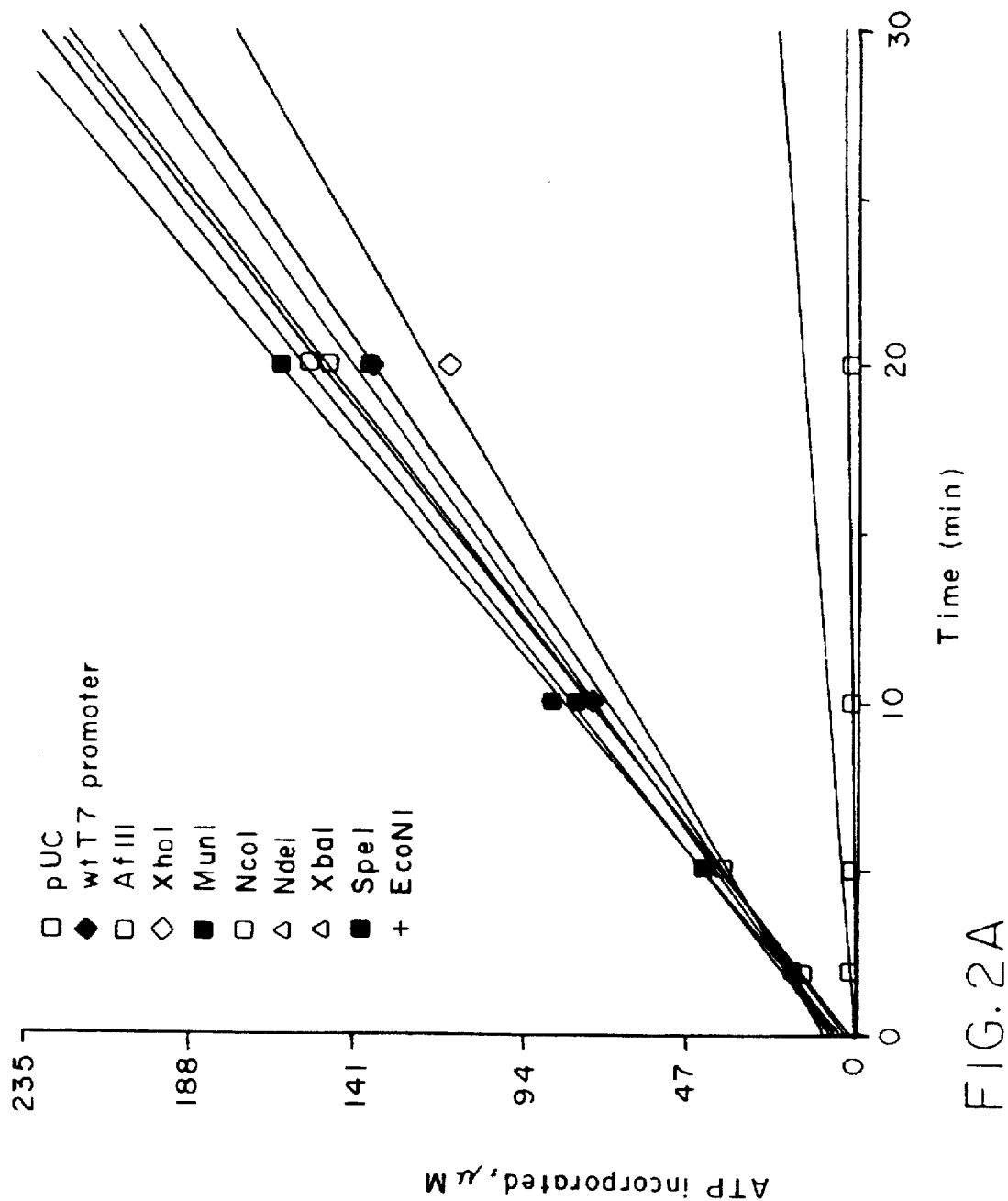
FIGS. 2A & 2B show the effect of supercoiling on in vitro transcription from wild-type and 8 mutant T7 promoters, each containing an introduced internal restriction site. Transcription reactions were carried out either with supercoiled (A) or HindIII 3':-linearized (B) pDEFEND1 template as described in Example I.

In order to assay the effect of the introduced mutations on promoter function, each mutant promoter was tested in in vitro transcription assays under limiting polymerase conditions (M. Chamberlin and T. Ryan, *The Enzymes* 15:87–108 (1982), the disclosure of which is hereby incorporated by reference herein). Interestingly, 7 of the 8 introduced sites had no effect on transcription from supercoiled templates, with transcription levels equivalent to (or reproducibly exceeding) wild-type levels (FIG. 2A, Table I). As expected, the EcoNI promoter had activity only slightly higher than background. Given the high processivity of T7 RNA polymerase (Chamberlin, supra), however, the use of a circular template makes it difficult to quantitatively correlate observed incorporation levels with diminished promoter function, since a single initiation event leads to production of a very long transcript, of variable length.

Figure 2B:
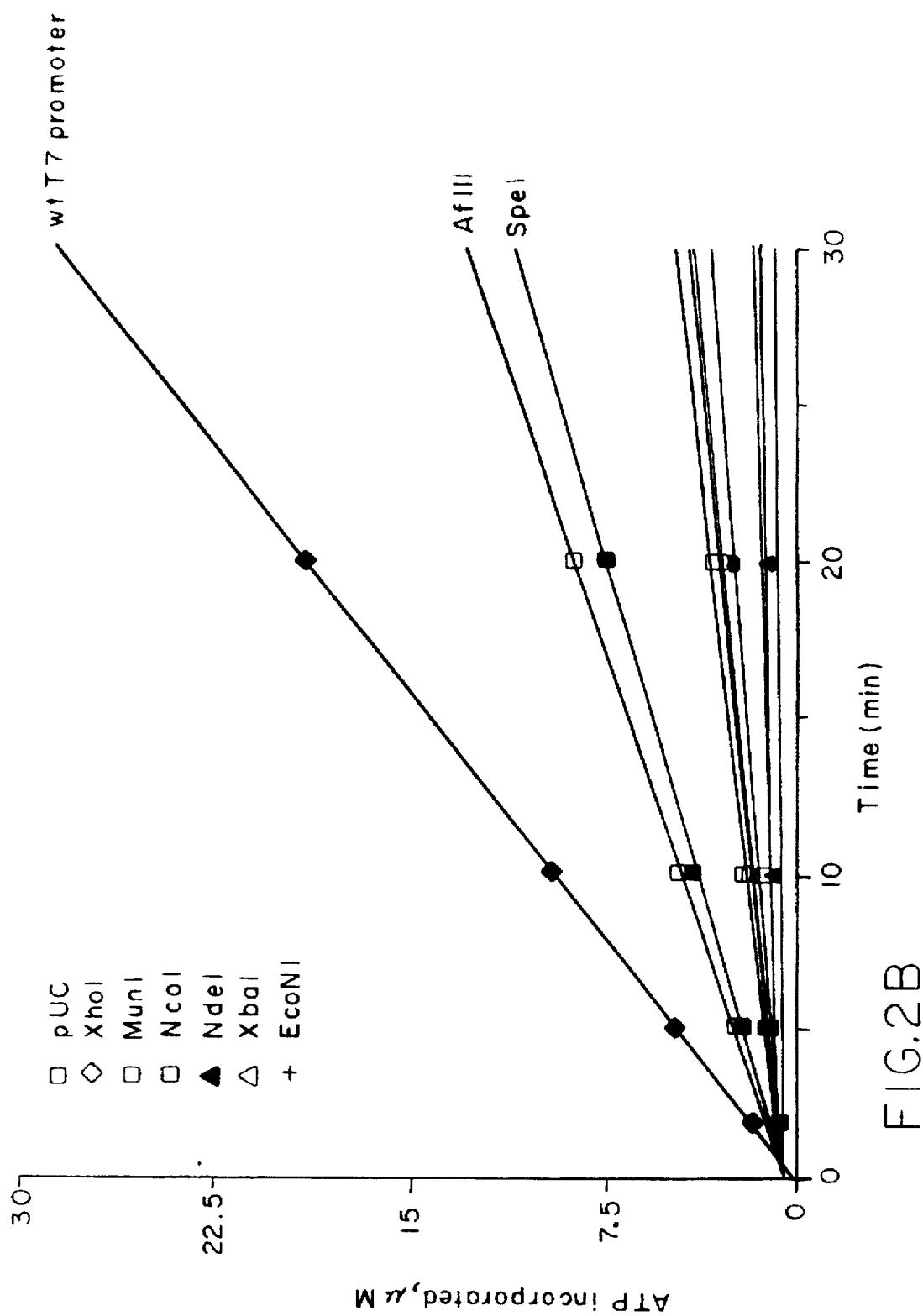
Figure 3:
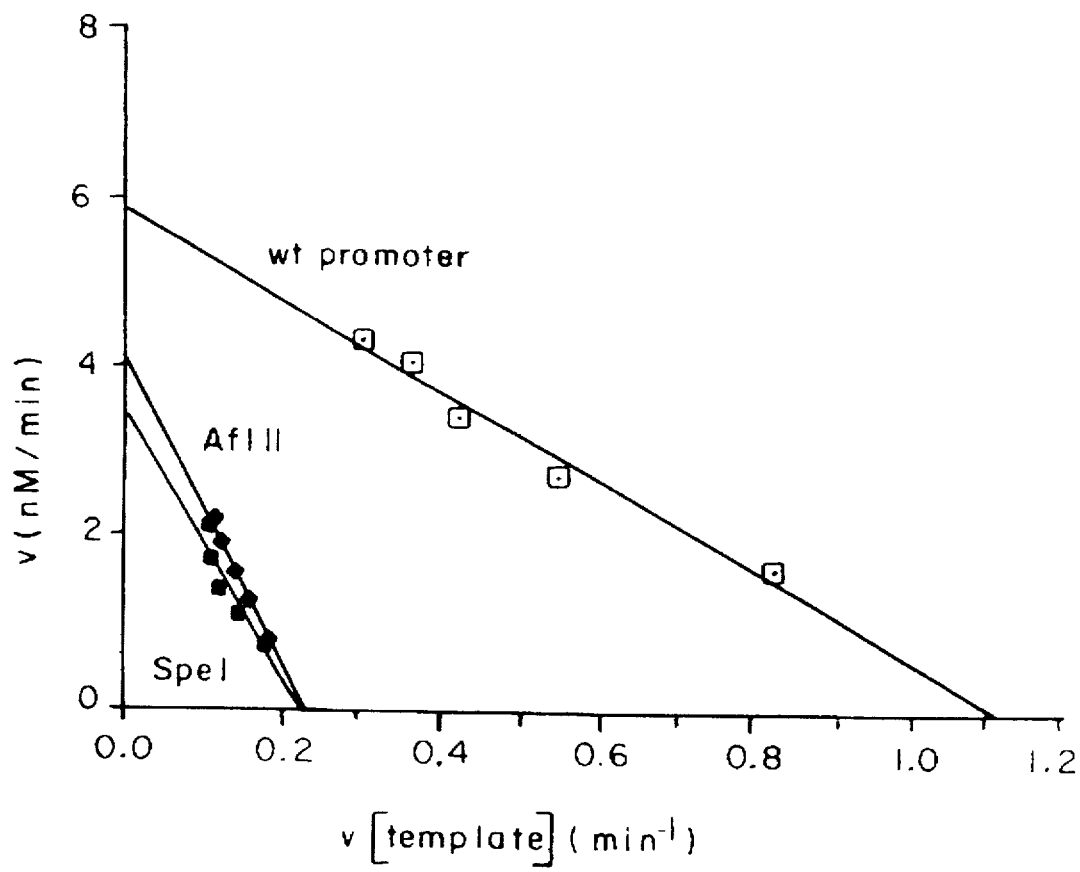
FIG. 3 is an Eadie-Hofstee plot showing steady-state Michaelis-Menton kinetics of in vitro transcription from the wild-type, AflIII, and SpeI T7 promoters. Transcription reactions were carried out with HindIII-linearized pUCT7, pUCT7(Afl) or pUCT7(Spe), at 0.4 nM T7 RNA polymerase and the indicated concentrations of template. The Michaelis constant $K_M$ corresponds to the negative of the slope of each line, while the maximum velocity $V_{max}$ is the y-intercept. The turnover number $k_{cat}$ is calculated from $V_{max}$ by dividing by the enzyme concentration (0.4 nM).
Figure 4A:
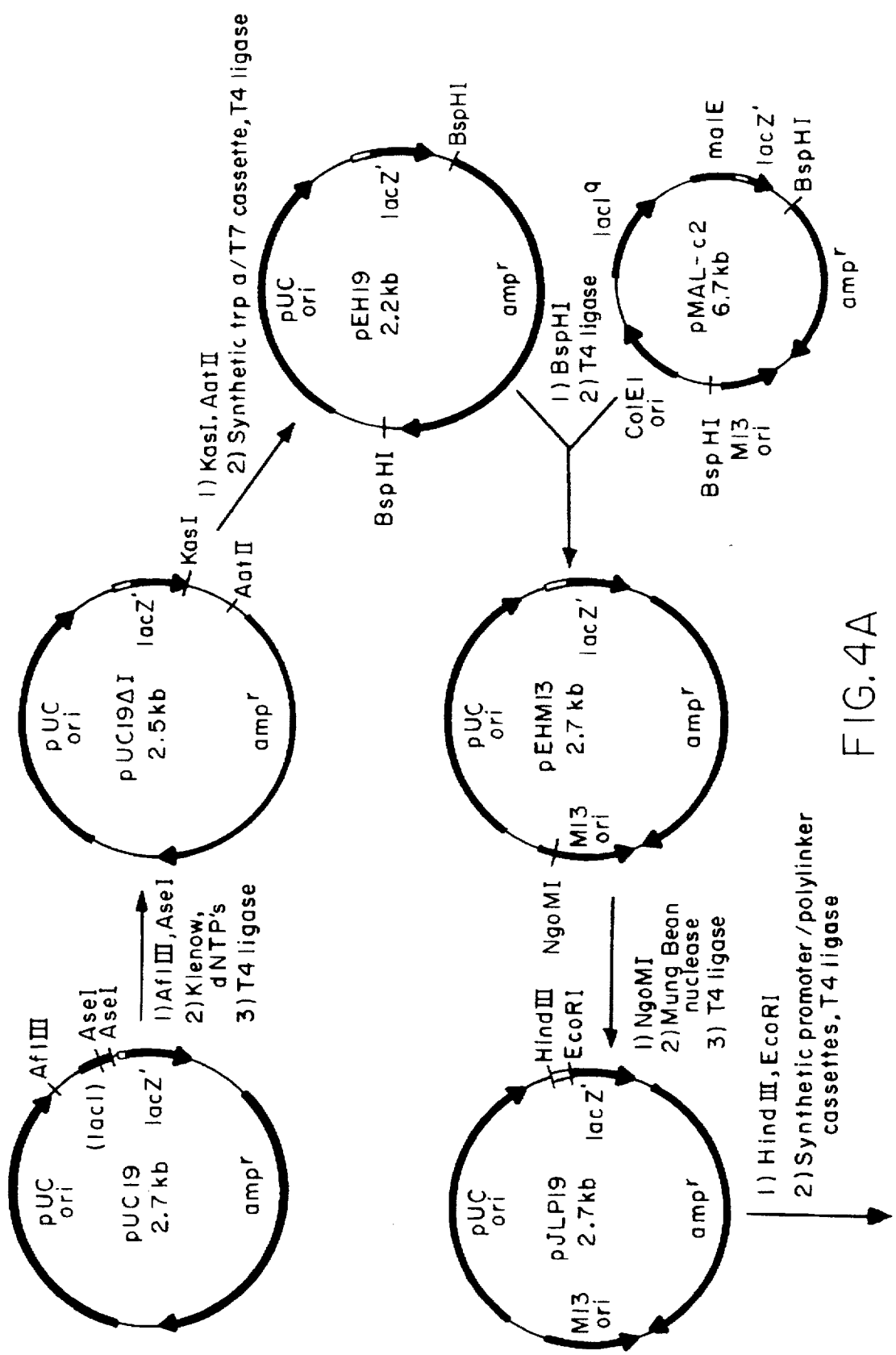
FIG. 4 summarizes the construction of the LITMUS vectors, as detailed in Example 2.
Figure 4B:
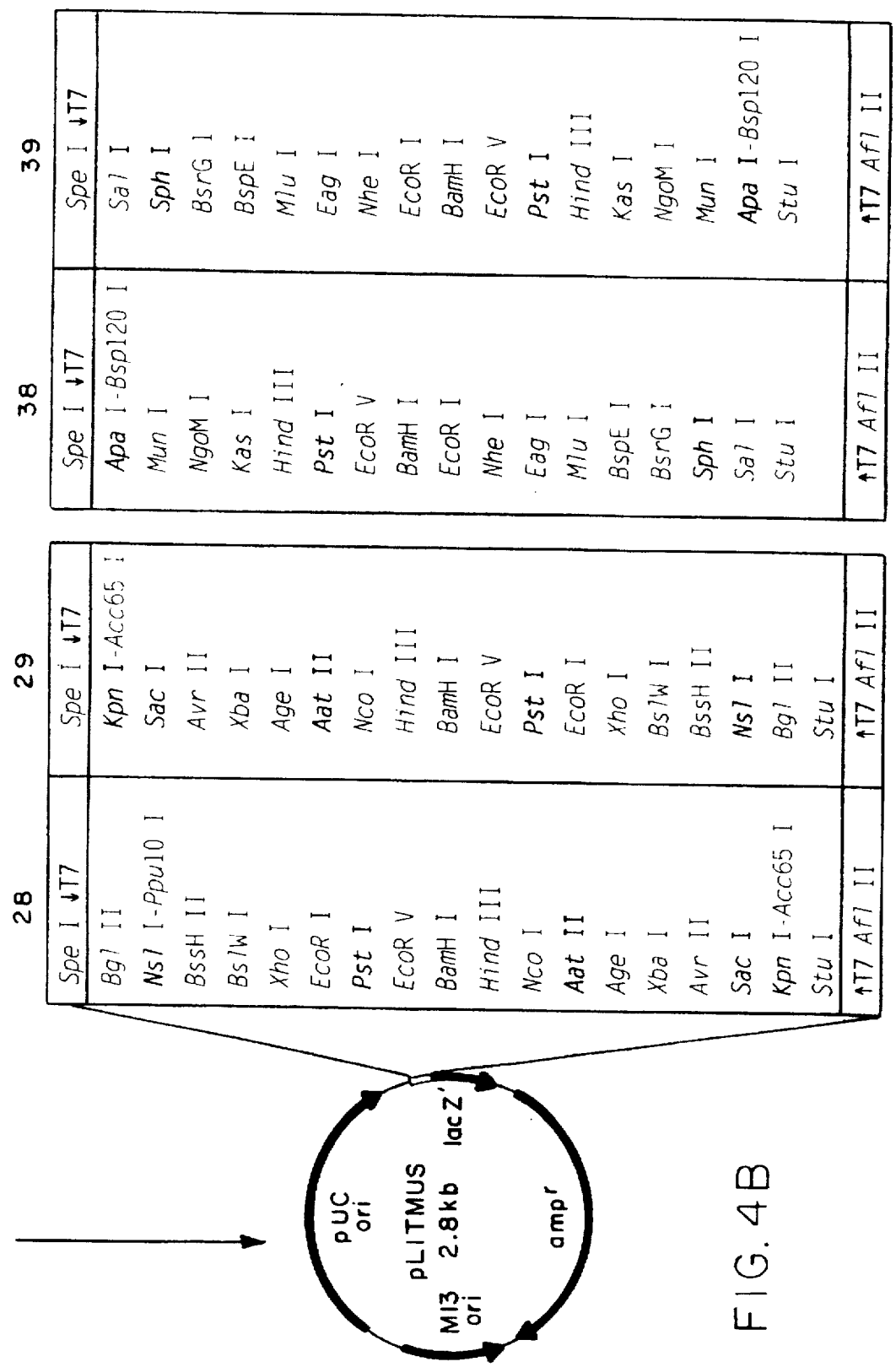

Consequently, all 8 mutations were assayed on templates that were linearized such that the resulting transcript is only 91 nucleotides in length (FIG. 2B, Table I). Under these conditions, the activities of the mutant promoters were markedly diminished. The AflII and SpeI promoters were only 44% and 35% as active as the wild-type promoter, respectively, with the others approaching background levels (Table I). This dramatic differential effect of supercoiling is consistent with the role of the mutagenized region in promoter melting rather than polymerase recognition (Chapman (1988) supra). Since initiation involves physically melting apart the strands to form the open complex (R. Strothcamp, et al., *Biochemistry* 19:1074–1080 (1980), the disclosure of which is hereby incorporated by reference herein), the energy of negative supercoiling (topologically equivalent to partially melted DNA) can be utilized to melt less-than-optimum sequences. Without this potential energy, only the wild-type sequence is efficiently melted by the polymerase, mutant promoters were digested with their cognate restriction enzymes. When the linearized plasmids were used as templates in in vitro transcription reactions, no incorporation of radiolabel above background was observed, as expected. Characterization Of The Most Active Mutations In order to rule out competition from weak SP6 promoter binding when further characterizing T7 RNA polymerase-mutant promoter interactions, the wild-type and AflII and SpeI mutant promoters were transferred into pUC19 by replacing the 377-bp AflIII-BamHI of pUC18 with the corresponding 417-bp fragments of wild-type and mutant pDEFEND1 to yield pUCT7, pUCT7(Afl) and pUCT7(Spe). Linearization of these constructs with HindIII yielded transcripts of comparable size to HindIII-linearized pDEFEND1. Steady-state kinetic analysis of HindIII-linearized pUCT7, pUCT7(Afl) and pUCT7(Spe)(FIG. 3) demonstrated that introduction of the AflII and SpeI sites had little effect on $k_{cat}$, but an approximate 3-fold increase in $K_M$ (i.e., 3-fold weaker binding assuming that $K_M$ represents a promoter dissociation constant). Given that the extension rate of T7 RNA polymerase is approximately 100 nucleotides/sec (Chamberlin, supra) and the transcript in these experiments is only 91 nucleotides long, the $k_{cat}$ of 10–15 min$^{-1}$ is consistent with transcriptional initiation being the rate-determining step, rather than chain elongation. Since mutations in the initiation region affect $K_M$ rather than $k_{cat}$, alteration of the nucleotide sequence in this region therefore affects a step along the initiation pathway intermediate between promoter binding and the rate-determining initiation step. The observation that the mutations have no effect on transcription from supercoiled DNA suggests that these substitutions exert their effect at the strand melting step.
Construction Of LITMUS Vectors In accordance with one preferred embodiment, in order to more fully exploit available restriction enzymes, it is desirable to eliminate as many nondegenerate 6-base restriction sites (with 4 base overhangs) from the pUC19 backbone (C. Yanisch-Perron, et al., *Gene*, 33:103–119 (1985)) as possible. At the same time, non-essential backbone regions are preferably deleted while introducing a filamentous phage origin for single-stranded DNA production (FIG. 4). For example, in one preferred embodiment, the 231-bp AflIII-Ase33 fragment of pUC19, containing a short remnant of the lacI gene, was deleted, resulting in pUC19ΔI. This renders the PvuII site within lacZα unique, allowing blunt-ended cloning at that site with blue-white screening.

Figure 6:
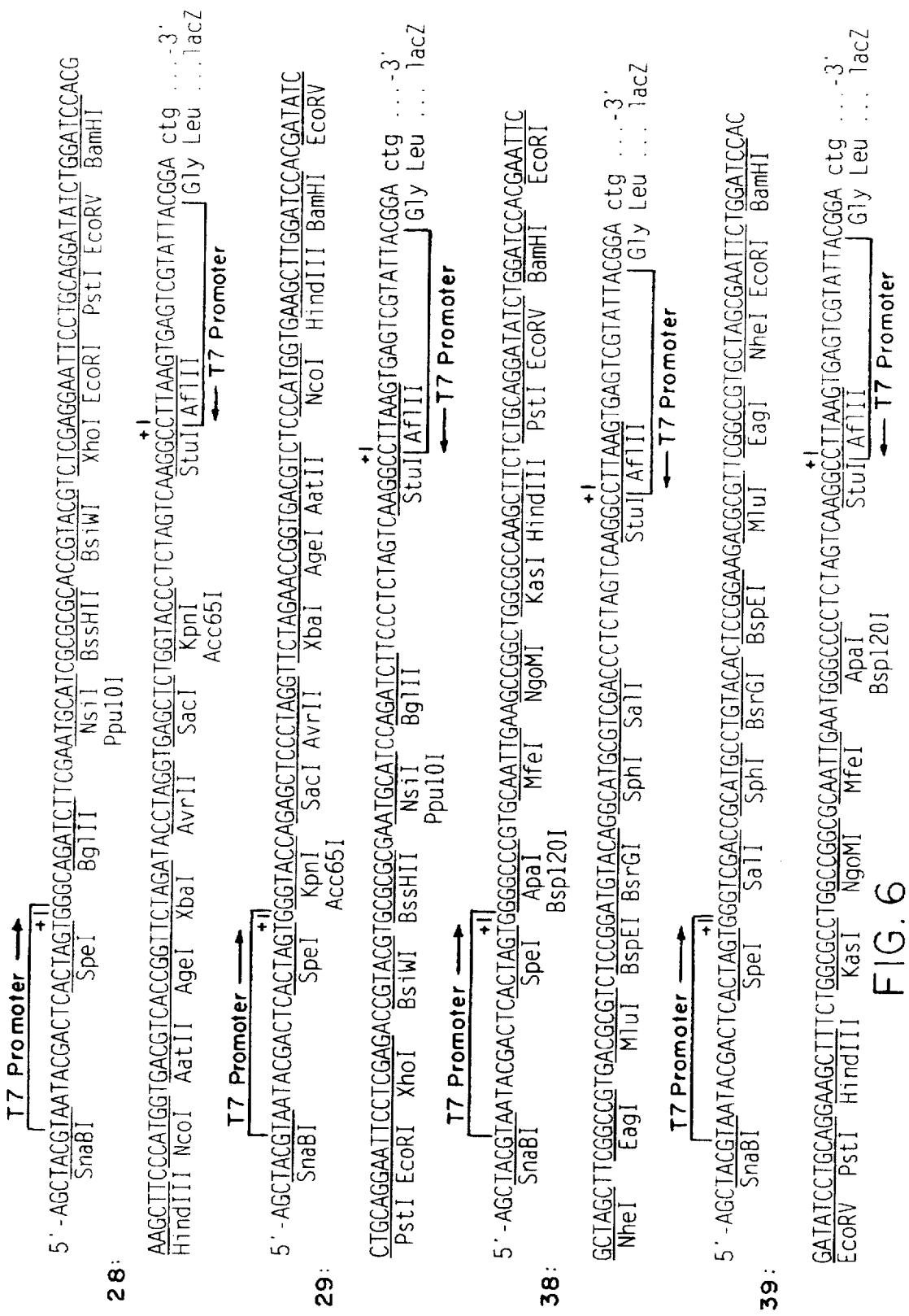
FIG. 6 shows the LITMUS polylinker sequences (SEQ ID NO:1, SEQ ID NO:2, SEQ ID NO:3, and SEQ ID NO:4). Restriction sites are underlined. Modified T7 promoters are indicated by brackets, with the first transcribed based denoted by "+1". Lower case bases indicate beginning of native lacZ sequence. The sequences shown are the complements of the strands that are packaged upon superinfection with M13 helper phage.

During the original construction of the pUC vectors (J. Vieira and J. Messing, *Gene*, 19:259–268 (1982), the disclosure of which is hereby incorporated by reference herein), the lacZα sequence up to Arg59 (A. Kalnins, et al., *EMBO J.*, 2:593–597 (1983), the disclosure of which is hereby incorporated by reference herein) was inadvertantly fused to an additional 29 vector-encoded residues ending with the amber codon TAG. Amber suppression in most commonly used cloning strains results in fusion of a further 15 residues to the α-peptide. In order to potentially increase the efficiency of α-complementation, a synthetic cassette containing defined transcriptional and translational termination Polylinker Design The main objective during the design of the polylinkers for the vectors of the present invention is to maximize possible cloning strategies. In certain preferred embodiments, the most useful restriction enzymes for cloning and subcloning preferably have non-degenerate 6-base pair specificities and yield 4-base 5' or 3' overhangs. For example, a set of 29 unique restriction sites, recognized by enzymes of this type, was divided among 2 polylinkers, designated 28 and 38 (FIG. 6). An additional 2 polylinkers, 29 and 39, have the same sites in the opposite order relative to lacZα, but have slightly different sequences to avoid rare *E. coli* codons. Sites for enzymes with compatible ends for ligations (e.g., XhoI and SalI) are placed in different polylinkers where possible. Sites for the enzymes BspHI and ApaLI are preferably not included, since both cut within the β-lactamase gene. All sites are distributed around a central "core" of sites for five commonly used (and inexpensive) enzymes: BamHI, EcoRI, EcoRV, PstI, and HindIII.

Additionally, the polylinkers used in the vectors of the present invention preferably contain three blunt-cutting enzyme sites: an EcoRV site in the middle of each

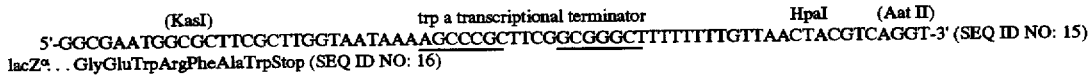

(KasI)    trp a transcriptional terminator    HpaI    (Aat II)
5'-GGCGAATGGCGCTTCGCTTGGTAATAAAAGCCCGCTTCGGCGGGCTTTTTTTTGTTAACTACGTCAGGT-3' (SEQ ID NO: 15)
lacZα...GlyGluTrpArgPheAlaTrpStop (SEQ ID NO: 16)

signals is introduced between the KasI and AatI sites of pUC19ΔI to yield pEH19. This eliminates the non-lacZ-derived codons, and adds an additional 3 wild-type lacZ residues and the strong stop signal TAATAA to the end of the gene. In addition, the cassette introduces a modified trp a/T7 transcriptional terminator sequence (G. Christie, et al., *Proc. Natl. Acad. Sci. USA*, 78:4180–4184 (1981), the disclosure of which is hereby incorporated by reference herein) to constrain P_{lac}-directed expression to the polylinker-lacZα segment of the vector. Addition of the terminator cassette, however, does not improve the intensity of the blue color on X-Gal indicator plates, indicating that fusion of 29 or 44 non-lacZ residues to the pUC α-fragment does not have a deleterious effect on α-complementation. However, the reported toxicity (P. Karlovsky and H. Prell, *Nucleic Acids Res.* 15:6753 (1987)) of the original pUC α-fragment (which results in small colonies when the polylinker is uninterrupted) was not observed in strains containing vectors of the present invention.

Figure 5:
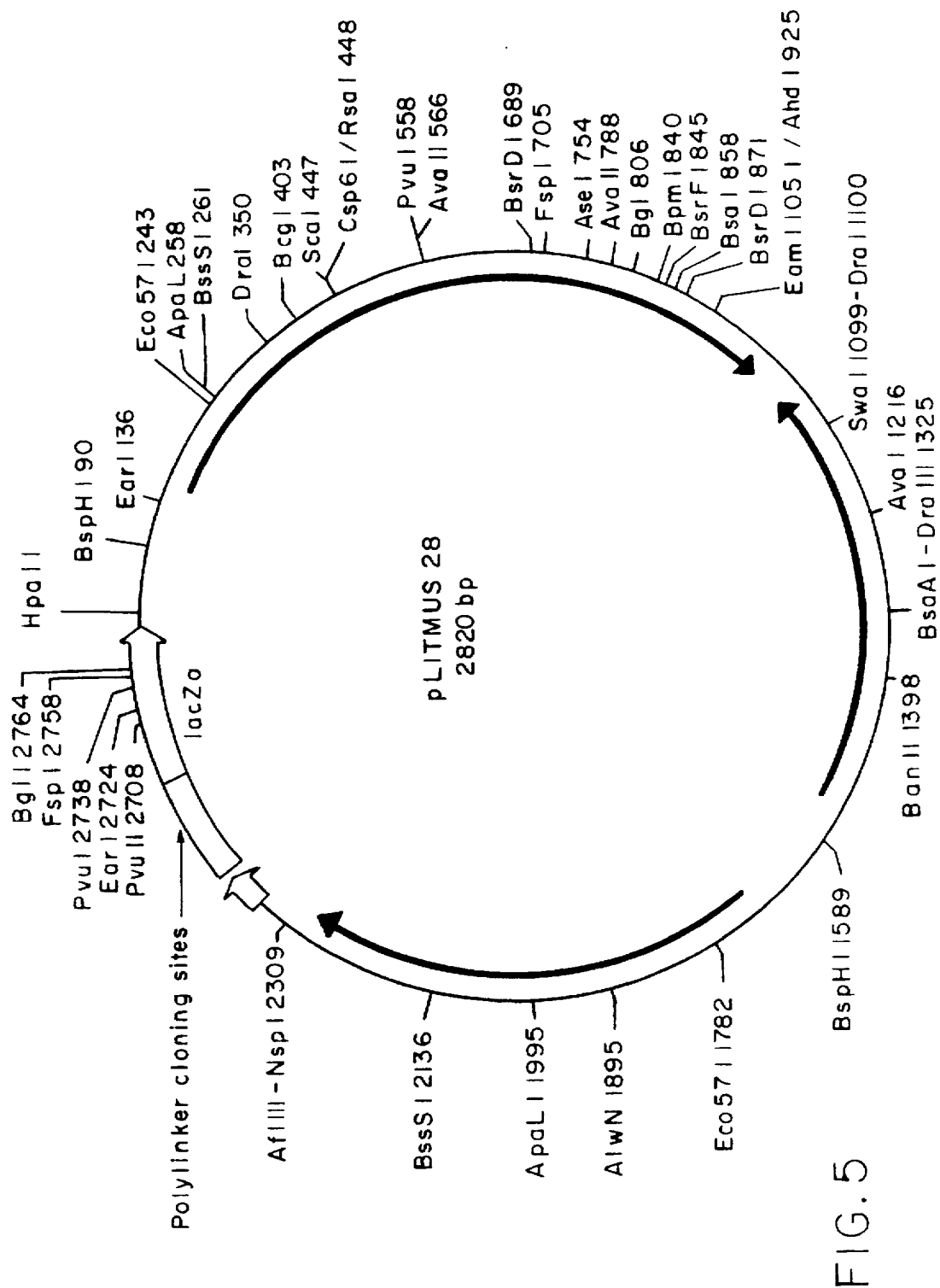
FIG. 5 is a map of LITMUS 28. Numbering begins at the first nucleotide of the unique HpaI site (introduced immediately downstream from the lacZα stop codon) and proceeds clockwise. The M13 origin is oriented such that the anticodon strand of $amp^r$ and lacZα (5' to 3' in a counterclockwise direction) is packaged upon superinfection.

In order to facilitate single-stranded DNA production for in vitro mutagenesis or sequencing, the M13 origin of replication (R. Zagursky and M. Berman, *Gene*, 27:183–191 (1984), the disclosure of which is hereby incorporated by reference herein) is preferably introduced, in a single orientation between the β-lactamase gene and the ColE1 origin, by replacing the 1008-bp BspHI fragment of pEH19 (above) with the corresponding 1503-bp segment from the expression phagemid pMAL-c2 (P. Riggs, *Current Protocols in Molecular Biology*, New York: Greene Publishing and J. Wiley & Sons, pages 16.6.1–16.6.14 (1992), the disclosure of which is hereby incorporated by reference herein). The NgoMI site within the M13 origin is eliminated by cleaving the resulting vector with NgoMI, treating the ends with mung bean nuclease, and religating to yield the fully modified vector backbone (FIG. 5). This modification has no effect on single-stranded DNA production upon superinfection with M13 helper phage, indicating a fully-functional M13 origin.

polylinker, and SnaBI and StuI sites at either end. This arrangement serves 2 purposes: the blunt sites at either end allow the polylinkers (with a single T7 promoter) to be easily transferred to other vectors, and the central EcoRV site provides an alternative to synthetic linker addition. Following cloning of blunt-ended fragments into the EcoRV site, excision of the insert at flanking sites produce a DNA fragment with 2 different sticky ends, allowing directional cloning in a subsequent step. Finally, sites for enzymes that yield a 3' overhang upon cleavage (PstI, NsiI, AatII, SacI, KpnI, ApaI and SphI) have been evenly distributed within the polylinkers. Since 3' overhangs are resistant to the action of exonuclease III, this arrangement allows generation of unidirectional nested deletions of cloned inserts with exonuclease III and mung bean nuclease (Slatko, et al., *Current Protocols in Molecular Biology*, New York: Greene Publishing and J. Wiley & Sons, pages 7.2.1–7.2.20 (1991), the disclosure of which is hereby incorporated by reference herein). This permits sequencing of long inserts without "primer walking."

The polylinker regions of the vectors of this invention are preferably fused to lacZα to facilitate blue-white screening, so the reading frame of each restriction site is chosen to minimize rare *E. coli* codons. Additionally, the polylinker sequences are carefully adjusted to exclude overlapping dam/dcm sites, inverted or direct repeats, long runs of a single base, and long runs of encoded hydrophobic or charged amino acids. Sites are preferably placed such that the recognition sequences do not overlap in order to permit double digests at adjacent sites. Most of the possible double digests at adjacent sites in the vector of the insert invention have been carried out, and in only a few cases is there insufficient spacing between sites for both enzymes in cleave to completion (R. Moreira and C. Noren, *Biotechniques* 19 (1995), the disclosure of which is hereby incorporated by reference herein).

Bidirectional RNA Probe Production With A Single RNA Polymerase

In a preferred embodiment, the polylinker region is flanked by two modified RNA polymerase promoters such as the T7 RNA promoter, each containing a unique restriction site that has been engineered into the consensus T7 promoter sequence (FIG. 6). Other RNA promoters such as the bacteriophage T3, SP6, K11 or BA14 promoters, or any eubacterial, archaeal or eukaryotic promoter, may also be used provided that it can be demonstrated, using the methods of the current invention (Example I and above), that i) cleavage within the promoter sequence inactivates the promoter and ii) any sequence modification necessary to incorporate the restriction site does not have a deleterious effect on transcription initiation from that promoter. Selective unidirectional transcription from one promoter is achieved by simply cleaving the other at an internally engineered restriction site. Since efficient labeling of RNA probes requires that the template be linearized at a site downstream from the insert prior to transcription anyway (Melton, supra), cutting at the site within the undesired promoter performs both functions in a single step. RNA probes corresponding to either strand of a cloned insert can thus be prepared, under identical conditions, using the inexpensive and well-characterized T7 RNA polymerase. This bypasses problems associated with other phage-encoded RNA polymerases (e.g., SP6 or T3), which have different optimum reaction conditions, and are often more expensive, more dilute, or less pure.

Introduction of an internal restriction site into each promoter necessitated altering the consensus promoter sequence. Specifically, for the T7 polymerase promoter, eight restriction sites were engineered into the initiation region (−1 to −6) of the T7 late promoter consensus sequence, since this region is the most tolerant of point mutations (Chapman, et al., *Nucl. Acids Res.*, 16:4511–4524 (1988), the disclosure of which is hereby incorporated by reference herein), and the activity of each mutant promoter was assayed (Example I, FIG. 2, Table I). The AflIII ($T_{-2} \rightarrow A$, $A_{-3} \rightarrow T$) and SpeI ($A_{-1} \rightarrow T$, $T_{-2} \rightarrow G$) promoters were the most active, and were introduced on either site of the LITMUS polylinkers (FIG. 6). Transcription of a cloned insert from the AflIII promoter is achieved by digesting with SpeI prior to in vitro transription, and vice-versa (FIG. 7). If the cloned insert contains SpeI or AFIII sites close to what would be the 5' end of the transcript, each promoter can alternatively be inactivated by cleavage at the polylinker site immediately downstream from that promoter (BglII, Acc65I, Bsp120I, or SalI can be used to inactivate the SpeT promoter in LITMUS 28, 29, 38 and 39, respectively; StuI will inactivate the AflII promoter in all 4). These enzymes leave blunt ends or 5' extensions, since promoter-independent transcription can initiate from 3' extensions (E. Schenborn and R. Mierendorf, *Nucl. Acids Res.*, 13:6223–6236 (1985), the disclosure of which is hereby incorporated by reference herein). Neither promoter is as strong as the unmodified T7 promoter under polymerase-limiting conditions (500 μM each NTP): the AflII promoter is <45% as active as the native promoter, while the SpeI promoter is somewhat weaker (FIG. 8). Kinetic analysis indicated that the introduced sites raise $K_M$ for template DNA, with little effect on $k_{cat}$ (FIG. 3). However, under conditions where one NTP is limiting (i.e., RNA probe conditions where the labeled nucleotide is at 1–2 μM), both modified promoters perform as well as the wild-type promoter (FIG. 8). This results in production of RNA probes of the highest possible specific activity. Preparative-scale transcription reactions (i.e., all 4 NTPs in excess) with LITMUS require that more T7 RNA polymerase be added (up to 20,000 units/mL) before yields approach that obtained using a wild-type T7 promoter vector, although the low cost and high available concentrations of the enzyme partially alleviate this problem. Furthermore, the presence of two opposing T7 promoters prevents the use of LITMUS as an in vivo expression vector in T7-based systems, unless one of the promoters has been excised. Thus, the intended use of the opposing T7 promoter system in LITMUS, as with other dual promoter vectors, is for production of RNA probes in vitro, since either modified promoter performs equivalently to the wild-type promoter when one of the NTPs is limiting (FIG. 8).

Southern Blotting With LITMUS RNA Probes

In order to test the sensitivity of Southern hybridization with RNA probes prepared from a clone produced using the vectors of the present invention, a 780-base pair EcoRI fragment of *Dirofilaria immitis* (a filarial parasite) cDNA, containing the 3' half of the nuclear hormone receptor 3 gene (dinhr3-3'), was cloned in both LITMUS 39 and a commercially available wild-type T7 promoter vector, pBluescript™ SK(−) (Stratagene, La Jolla, Calif.). Clones were selected in which the insert orientation relative to the T7 promoter in Bluescript matched the orientation relative to the SpeI-containing T7 promoter in LITMUS, so that the two probe sequences would match when transcription was from the weaker SpeI promoter of LITMUS. RNA probes were prepared from both vectors under identical transcription conditions, and equivalent levels of [$^{32}$P]-ATP incorporation were observed for each. Both RNA probes as well as a DNA probe prepared from the same insert by random priming with Klenow fragment (Feinberg and Vogelstein, *Anal. Biochem.*, 132:6–13 (1983)), were hybridized to identical blots of EcoRI-digested *D. immitis* genomic DNA (FIG. 9). Insert-containing vector DNA (39dinHr3-3') and *Streptococcus albus* genomic DNA were also included on each blot as positive and negative controls, respectively. As expected, none of the probes hybridized to the *S. albus* DNA, but all three hybridized equally well to the expected 1800-bp EcoRI fragment of *D. immitis* DNA (dinhr3 contains several introns (C. Maina, unpublished observations)). Interestingly, at identical hybridization temperatures (65° C.), both RNA probes gave cleaner signals than the DNA probe, which hybridized to a number of higher molecular weight fragments (FIG. 9, last lane). As expected, RNA probes synthesized from LITMUS hybridize with equivalent sensitivity to probes synthesized from other vector systems when Southern blotting single-copy genes in eukaryotic genomic DNA.

The following Example are given to illustrate embodiments of the present invention as it is presently preferred to practice. It will be understood that these Examples are illustrative, and that the invention is not to be considered as restricted thereto except as indicated in the appended claims.

EXAMPLE I

Introducing Internal Restriction Sites into the T7 Promoter

Enzymes and reagents. T7 RNA polymerase, all restriction enzymes, and enzymes for Kunkel and Eckstein mutagenesis were from New England Biolabs (Beverly, Mass.) ("NEB"). Other reagents were purchased from the indicated suppliers. Oligonucleotides were synthesized on 0.04–0.2 μmol scale by the Organic Synthesis Group of New England Biolabs and were purified either by reverse-phase chromatography on C-18 Sep-Pak columns (Waters) or denaturing polyacrylamide gel electrophoresis (PAGE) prior to use. Synthetic duplexes were annealed at a concentration of 2 μg/10 μL in 10 mM Tris-HCl, pH8.0, 1 mM EDTA, 100 mM NaCl, by heating to 90° C. and slowing cooling to <30° C.

Plasmids and strains. Plasmids were propagated in *E. coli* NM522 (F′ lacI$^q$Δ (lacZ)M15 proA$^+$B$^+$/supE thiiΔ(lac-proAB) Δ(hsdMS-mcrB)5) or ER2267 (F′ lacI$^q$Δ(lacZ)M15 proA$^+$B$^+$zzf:mini-Tn10/endA1 recA1 e14 supE44 thi-1 Δ(mcrC-mrr) 114::IS10 Δ(argF-lac)U169). Single-stranded phagemid DNA for Kunkel mutagenesis was isolated from CJ236 (F′ cat/dut ung1 thi-1 relA1 spoT1 mcrA) following superinfection with M13K07 as described (J. Vieira and J. Messing, *Methods Enzymol.* 153:3–11 (1987), the disclosure of which is hereby incorporated by reference herein). The pUC18 derivative pDEFEND1 was constructed as follows: The BsaI site (position 1766 in pUC18) in the β-lactamase gene was removed by Eckstein mutagenesis (K. L. Nakamaye and F. Eckstein, *Nucleic Acids Res.* 14:9679–9698 (1986), the disclosure of which is hereby incorporated by reference herein), using the single-stranded form of the pUC phagemid derivative pBluescript™ SK-(Stratagene, La Jolla, Calif.) and the mutagenic primer 5′-pTGAGCGTGGTTCTCGC GGT-3′ (SEQ ID NO:17) (introduced mutation in bold). This mutation was then transferred into pUC18 by replacing the 562-bp Cfr10T-AlwNI fragment of pUC18 with the identical fragment (but lacking the BsaI site) from mutagenized Bluescript. The resulting construct (pUC18BsaI⁻) was digested with EcoRI and HindIII and the following synthetic duplex was inserted (solid underlined bases indicate T7 consensus late promoter sequence, dotted underlined sequences indicate consensus SP6 promoter):

In order to rule out competition from weak SP6 promoter binding when further characterizing T7 RNA polymerase-mutant promoter interactions, the wild-type and AflII and SpeI mutant promoters were transferred into pUC19 by replacing the 377-bp AflIII-BamHI of pUC18 with the corresponding 417-bp fragment of pDEFEND1 to yield pUCT7, pUCT7(Afl) and pUCT7(Spe).

In vitro transcription. Plasmid templates were purified by alkaline lysis and ultracentrifugation in CsCl gradients prior to in vitro transcription reactions. For linear templates, DNA was digested with HindIII (for assaying intact promoters) or the appropriate enzyme for cleaving within each promoter in 100–500 μL reactions containing 100 μg/mL DNA and 10 units enzyme per μg of DNA. Linearized DNA was purified from restriction digests by phenol:chloroform extraction and ethanol precipitation, and then requantitated by A$_{260}$. Transcription reactions (50 μL) contained 40 mM Tris-HCl, pH 7.5; 5 mM NaCl; 6 mM MgCl$_2$; 10 mM DTT; 2 mM spermidine; 100 μg/mL BSA: 10 units RNasin™ (Promega, Madison, Wis.); 0.5 mM each GTP, CTP, UTP; 0.1 mM α-[$^{32}$P]-ATP (2–10 μCi/nmol, DuPont/NEN); 2 μg supercoiled or linear DNA; and 25 units T7 RNA polymerase (NEB); and were incubated at 37° C. Aliquots (7 μL) were withdrawn at 5 minute intervals for 30 minutes, combined with equal volumes of 50 mM EDTA, pH 8.0, 1 mg/mL yeast tRNA (Boehringer-Mannheim, Germany), and spotted on Whatman 3 MM paper squares. Filters were washed 4×20 minutes in ice-cold 10% trichloroacetic acid, 2×10 minutes

```
                  EcoRI                            HindIII
5'AATTATAATACGACTCACTATAGGGAGACCGAATTCGCAAGCTTGCGTCATCCTATTCTATAG
3'     TATTATGCTGAGTGATATCCCTCTGGCTTAAGCGTTCGAACGCAGTAGGATAAGATATC TGTCACCTAAATCGTATGGT      -3'(SEQ ID NO:18)
ACAGTGGATTTAGCATACAATCGA-5'(SEQ ID NO:19)
```

Figure 1:
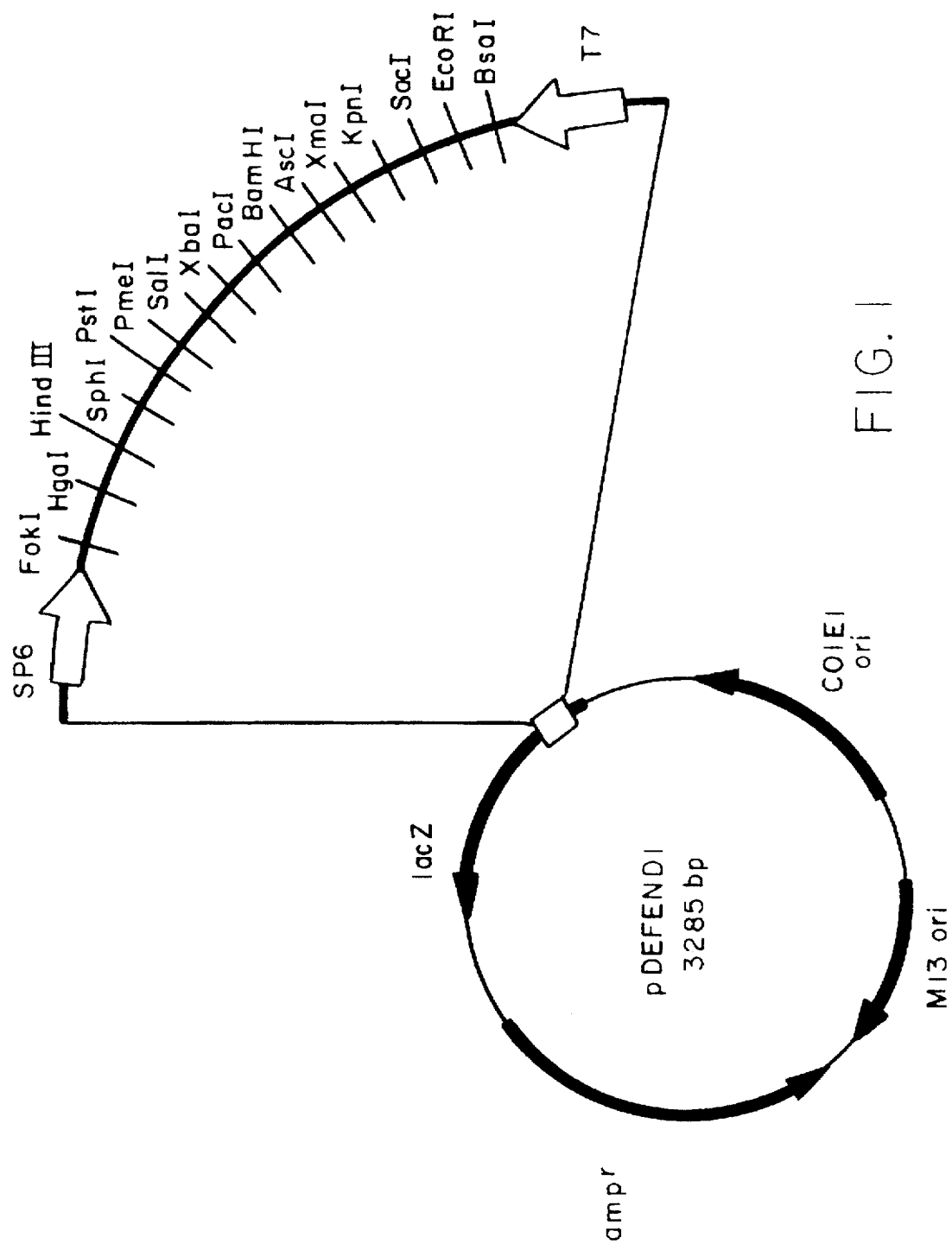
FIG. 1 is a map of the vector pDEFEND1, utilized for testing mutant T7 promoters.

This construct (pII-47) was then digested with EcoRI and HindIII and the polylinker region (the 79-bp EcoRI to HindIII fragment) of pNEB193 (New England Biolabs, Beverly, Mass.) was inserted. Finally, to permit isolation of single-stranded DNA for promoter mutagenesis, the M13 origin was inserted by replacing the 477-bp Eam1105I-AlwNI fragment with the analogous 974-bp fragment (containing the M13 origin) of pMAL-p2 (Riggs, supra), yielding pDEFEND1 (FIG. 1). Restriction sites were then introduced into the T7 promoter of pDEFEND1 by Kunkel mutagenesis (T. Kunkel, *Proc. Natl. Acad. Sci. USA* 82:488–492 (1985), the disclosure of which is hereby incorporated by reference herein) using the following oligonucleotides (bases in bold denote restriction sites, underlined bases indicate introduced mutations):

in ethanol, dried and counted in a liquid scintillation counter. K$_M$ and k$_{cat}$ values were calculated from Eadie-Hofstee plots of initial rates (incorporation plots were typically linear from 0–25 minutes) determined at 0.4 nM enzyme and 2–20 nM HindIII-linearized pUCT7, pUCT7(Afl) and pUCT7 (Spe).

EXAMPLE II

Construction of LITMUS 28

By way of example, the construction of LITMUS 38 is provided in detail (FIG. 4). The construction of LITMUS 28, LITMUS 29 and LITMUS 39 are identical up to and including a common intermediate vector, pJLP19, and dif-

```
AflIII: 5'-pACGACTCACTTAAGGGAGACCG-3' (SEQ ID NO: 20)
XhoI:   5'-pACGACTCACTCGAGGGAGACCG-3' (SEQ ID NO: 21)
MunI:   5'-pTACGACTCACAATTGGGAGACCGA-3' (SEQ ID NO: 22)
NcoI:   5'-pTACGACTCACCATGGGGAGACCGA-3' (SEQ ID NO: 23)
NdeI:   5'-pTAATACGACTCACATATGGGAGACCGAATT-3' (SEQ ID NO: 24)
XbaI:   5'-pAATACGACTCTCTAGAGGGAGACCG-3' (SEQ ID NO: 25)
SpeI:   5'-pCGACTCACTAGTGGGAGACCGA-3' (SEQ ID NO: 26)
EcoNI:  5'-pGAATTATAATACGACTACTATAAGGAG-3' (SEQ ID NO: 27)
``` ferences after that point are limited to the sequences of the synthetic oligonucleotide cassettes utilized.

Reagents and General Methodologies. All restriction and DNA modifying enzymes were from New England Biolabs (Beverly, Mass.) (NEB) unless otherwise noted. Oligonucleotides were synthesized on 0.2 µmol scale by the Organic Synthesis Group of New England Biolabs and supplied crude. Synthetic oligonucleotides were purified on 8% denaturing polyacrylamide gels (1× TBE buffer) prior to use. Bands were visualized by UV shadowing, and DNA was eluted from excised minced bands by overnight soaking in 0.5M NH$_4$OAc, pH 8, 10 mM MgCl$_2$, 1 mM EDTA, 0.1% SDS at 37° C. with shaking. SDS was removed by phenol:chloroform extraction and oligonucleotides were phosphorylated with T4 polynucleotide kinase (J. Sambrook, E. Fritsch, T. Maniatis, *Molecular Cloning: A Laboratory Manual*, Cold Spring Harbor Laboratory Press:Cold Spring Harbor (1989), the disclosure of which is hereby incorporated by reference herein). Synthetic duplexes were annealed at a concentration of 2 µg/10 µL in 10 mM Tris-HCl, pH 8.0, 1 mM EDTA, 100 mM NaCl, by heating to 90° C. and slowing cooling to <30° C.

All plasmids were maintained in *E. coli* NM522 or ER2267 (see above), and were purified on large scale by alkaline lysis followed by CsCl ultracentrifugation (Sambrook, supra). Minipreps were carried out by the alkaline lysis method, with phenol:chloroform extraction and RNase treatment to remove contaminating protein and RNA. DNA restriction digests were carried out in 50 µL volumes containing 1 µg DNA in the recommended buffer for the enzyme being used. 4–20 units of enzyme were added, and reactions were incubated at 37° C. for 2–3 hours. Ligation reactions (20 µL) contained 40–100 ng cleaved vector DNA, a four-fold molar excess of insert (where applicable), and 400 NEB units of T4 DNA ligase, and were incubated overnight at 16° C. All other DNA modifying enzymes were used according to instructions provided by the manufacturers. Restriction fragments were purified by preparative agarose gel electrophoresis in TAE buffer (Sambrook, supra). Bands were visualized by ethidium staining, and DNA was eluted from excised bands by adding an equal volume of phenol, freezing at −70° C., centrifuging, and recovering DNA from the aqueous layer by ethanol precipitation.

Single-stranded DNA for mutagenesis was isolated from CJ236 (above) following superinfection with M13KO7 helper phage (Vieira, 1987, supra).

pUC19ΔI pUC19 (Yanisch-Perron, supra) was digested with AflIII, and the sticky ends filled in with Klenow fragment. Following digestion with AatII, the 1811-bp AflIII-AatII fragment was gel-purified. In a separate reaction, pUC19 was digested with AseI, filled in as before, digested with AatII, and the 645-bp AseI-AatII fragment was gel purified. The two fragments were ligated, with the net effect being deletion of the 231-bp AflIII-AseI fragment of pUC19, resulting in pUC19ΔI (2455 bp).

pEH19. pUC19ΔI was digested with KasI and AatII, the 2156-bp fragment was gel-purified, and the following synthetic duplex was inserted, yielding pEH19 (2211 bp):

```
       (KasI)                        transcriptional terminator                HpaI  (AatII)
5'-GCGCTTCGCTTGGTAATAAAGCCCGCTTCGGCGGGCTTTTTTTTGTTAACTACGT -3' (SEQ ID NO: 28)
3'-    AAGCGAACCATTATTTCGGGCGAAGCCGCCCGAAAAAAAACAATTGA       -5' (SEQ ID NO: 29)
``` pEHM13. pEH19 and pMAL-c2 (Riggs, supra) were each digested with BspHI. The 1213-bp fragment of pEH19 and the 1503-bp fragment of pMAL-c2 were gel-purified and ligated, yielding pEHM13 (2716 bp). Clones containing both fragments in the correct orientation were screened by digestion of miniprep DNA with PstI and NgoMI.

pJLP19. The NgoMI site within the M13 origin was eliminated by cleaving pEHM13 with NgoMI, removing the protruding 5' ends with 10 units of mung bean nuclease/0.5 µg DNA, and religating to yield pJLP19 (2712 bp).

LITMUS 38. The polylinker/promoter region of LITMUS 38 was built up by successive ligation of synthetic duplexes into pJLP19 as follows: pJLP19 was digested with HindIII and EcoRI, gel-purified, and the following synthetic duplex was inserted to yield pJLP38 (2760 bp):

```
(HindIII)  ApaI
5' AGCTGGGCCCGTGCAATTGAAGCCGGCTGGCGCCAAGCTTCTCTGCAGGATATCTGGATCC
3'-    CCCGGGCACGTTAACTTCGGCCGACCGCGGTTCGAAGAGACGTCCTATAGACCTAGG
                                                      BspEI  (EcoRI)
        ACGAATTCGCTAGCTTCGGCCGTGACGCGTCTCCGGA          -3' (SEQ ID NO: 30)
        TGCTTAAGCGATCGAAGCCGGCACTGCGCAGAGGCCTGTTAA -5' (SEQ ID NO: 31)
```

In a separate ligation, pJLP19 was digested with HindIII and EcoRI, gel-purified, and the following synthetic duplex was inserted to yield pEN38 (2755 bp):

```
         (HindIII)    T7>         SpeI      ApaI        BspEI
   5'-AGCTACGTAATACGACTCACTAGTGGGGCCCGTTAATCCGGATGTACAGGCATGC
   3'-      TGCATTATGCTGAGTGATCACCCCGGGCAATTAGGCCTACATGTCCGTACG
                                      AflII          <T7    (EcoRI)
             GTCGACCCTCTAGTCAAGGCCTTAAGTGAGTCGTATTAT    -3' (SEQ ID NO: 32)
             CAGCTGGGAGATCAGTTCCGGAATTCACTCAGCATAATATTAA -5' (SEQ ID NO: 33)
``` pJLP38 and pEN38 were each digested with ApaI and BspEI. The 2744-bp fragment of pEN38 was ligated to the 88-bp fragment of pJLP38 to yield LITMUS 38S (2832 bp).

In order to delete a fortuitous strong *E. coli* promoter sequence that arose during polylinker construction, Kunkel mutagenesis (Kunkel, supra) was carried out on single-stranded LITMUS 38S with the following mutagenic oligonucleotide (underlined bases denote introduced mutations), yielding LITMUS 38:

5'-GGCCTTAAGTGAGTCGTATTA CGGACTGGCCGTCGTTTTACAACG-3' (SEQ ID NO:34)

EXAMPLE III

Southern Blotting

For RNA probe production, the 780-bp *D. immitis* nHr3-3' EcoRI fragment was inserted into EcoRI-cut LITMUS 39 or Bluescript™ SK-(Stratagene, La Jolla, Calif.), yielding 39dinHr3-3' and SKdinHr3-3', respectively. Miniprep clones were selected in which the insert orientation relative to the T7 promoter in Bluescript matched the orientation relative to the SpeI-site-containing T7 promoter in LITMUS 39. Plasmid DNA for in vitro transcription was purified from *E. coli* NM522 (see above) by alkaline lysis and CsCl ultracentrifugation.

RNA probes were synthesized by in vitro transcription in 10 μL reactions containing 0.5 μg SpeI-cut SKdinHr3-3' or AflII-cut 39dinHr3-3' in 40 mM Tris-HCl, pH 7.5; 6 mM MgCl$_2$; 5 mM NaCl; 2 mM spermidine; 10 mM DTT; 0.1 mg/mL BSA; 0.5 mM each GTP, UTP and CTP; 40 μCi α-[$^{32}$P]-ATP (3000 Ci/mmol, New England Nuclear, Boston, Mass.); 20 units placental RNase inhibitor (RNAsin™, Promega, Madison, Wis.); and 50 units T7 RNA polymerase. Reactions were incubated 60 min. at 37° C., after which 1 unit DNase I (Promega, Madison, Wis.) was added and incubation was continued for an additional 15 min. Following addition of 10 μg yeast tRNA as carrier, reactions were diluted to 200 μL, extracted once with 1:1 phenol:chloroform, adjusted to 3M ammonium acetate, and ethanol precipitated. Probes were resuspended in TE buffer and used without denaturation. DNA probes were synthesized by random priming (Feinberg and Vogelstein, supra) of the gel-purified 780-bp EcoRI fragment of 39dinHr3-3' with the NEBlot™ system (New England Biolabs, Beverly, Mass.), using 50 μCi α-[$^{32}$P]-dATP (3000 Ci/mmol, New England Nuclear, Boston, Mass.). DNA probes were separated from unincorporated label by gel-filtration on a NICK™ column (Pharmacia, Piscataway, N.J.), and denatured immediately prior to addition to the membrane by boiling 5 min. and rapidly cooling. EcoRI-digested target DNA was electrophoresed on 1% agarose gels, denatured in 1.5M NaCl, 0.5N NaOH, neutralized in 1M Tris-HCl, pH 7.4, 1.5M NaCl, and transferred to nitrocellulose membranes (BA45, Schleicher & Schuell, Keene, N.H.) in 20× SSC. DNA was fixed to the membrane by baking (80° C., 2 h), after which membranes were pre-hybridized for 2 h at 65° C. in 0.1 mL/cm$^2$ of 6× SSC, 1% SDS, 0.1% Tween-20, 100 μg/mL yeast tRNA, 50% formamide (RNA probes), or 6× SSC, 0.5% SDS, 5×Denhardt's reagent, 100 μg/mL denatured salmon sperm DNA (DNA probes). Following addition of probe (10$^6$ cpm/mL), incubation at 65° C. was continued overnight. Membranes were washed in 1× SSC, 0.1% SDS for 30 minutes at room temperature (twice); 0.1× SSC, 0.1% SDS for 30 minutes at 65° C. (twice); and autoradiographed 2 days (−70° C., with intensifier screen).

EXAMPLE IV

LITMUS 28

Description

LITMUS 28 is a multi-purpose cloning/in vitro transcription phagemid vector. The molecule is a small double-stranded circle 2823 base pairs in length (molecular weight= 1.8×10$^6$ daltons).

The key features of this vector are:

- extensive set of restriction sites with unique 4-base overhangs in the polylinker
- blue/white selection
- high copy number (pUC origin)
- ampicillin resistance
- single-stranded (M13) origin
- opposing T7 promoters for making RNA probes from either strand (see below)
- compatible with pUC/M13 sequencing primers, as well as 4 new primers
- companion vector, LITMUS 29, has the same sites in opposite order.

It is supplied in 10 mM Tris-HCl (pH 8.0), 1 mM EDTA.

Polylinker Region

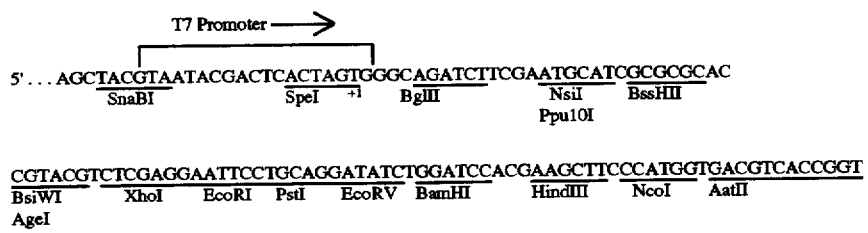

-continued

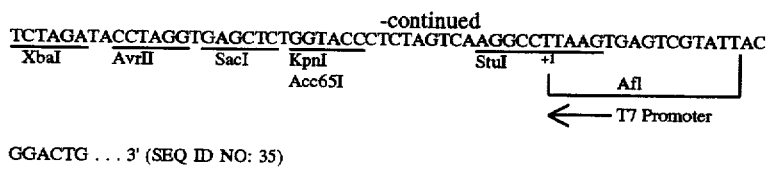

GGACTG . . . 3' (SEQ ID NO: 35)

Preparation:

LITMUS 28 is isolated from *E. coli* ER2267 by a standard plasmid purification procedure.

Note: Appropriate strains of *E. coli*-containing the LITMUS 28 plasmid form blue colonies on X-gal plates; when a fragment is inserted in the polylinker, the colonies are white. Blue/white selection is best achieved by plating on a rich media (e.g. LB) supplemented with X-gal (40 µg/ml) and IPTG (0.1 mM).

Production of RNA Probes from Inserts Cloned in LITMUS 28

Unlike other bidirectional transcription vectors, direction of transcription in LITMUS 28 is determined by which restriction enzyme is used to linearize the DNA template, rather than by which RNA polymerase is used. The downstream T7 promoter can be inactivated by digestion with AflIII for transcription off the upstream promoter; or the upstream T7 promoter is inactivated with SpeI for transcription off the downstream promoter. If the cloned insert contains sites for either enzyme close to the active promoter, BglII or StuI may be used in place of SpeI or AflIII, respectively.

Protocol:

1) Digest 2–5 µg insert-containing vector with appropriate enzyme for desired direction of transcription. Purify digested DNA by phenol extraction and ethanol precipitation. Suspend in TE to 1 µg/µl. Check recovery by minigel.

2) Set up transcription reactions at room temperature as follows:

| | |
|---|---|
| 10× RNA probe buffer | 1 µl |
| 100 mM DTT | 1 µ |
| 1 mg/ml BSA | 1 µl |
| Linearized DNA, 1 µg/µl | 0.5 µl |
| α-[$^{32}$P] rNTP, 3000 Ci/mmol (CTP, ATP, or UTP) | 4 µl (40 µCi) |
| 5 mM remaining 3 NTP's | 1 µl |
| Placental RNase inhibitor, 20–40 U/µl | 0.5 µl |
| T7 RNA polymerase, 50 U/µl | 1 µl |
| | 10 µl |

Incubate 60–90 min at 37°–40° C.

3) Add 1 unit RNase-free DNase, incubate 15 minutes at 37° C.

4) Dilute to 200 µl with TE, add 1 µl 10 mg/ml yeast tRNA (Sigma)

5) Extract once with 200 µl 1:1 phenol:chloroform. Tranfer upper layer to new tube 6) Add 100 µl 7.5M NH$_4$OAc, 600 µl ethanol, store at −20° C. 30 min 7) Pellet RNA in microfuge 8 min, air-dry briefly, resuspend in 200 µl 8) Add 50 µl 7.5M NH$_4$OAc, 500 µl ethanol and reprecipitate 9) Suspend pellet in 1 ml TE. Count 1–10 µl in scintillation counter. Final activity should be $10^7$–$10^8$ cpm/ml. Use probe within 1–2 days.

10× RNA probe buffer 400 mM Tris-HCl, pH 7.5, 50 mM NaCl, 60 mM MgCl$_2$, 20 mM spermidine Membrane Hybridization with RNA Probes:

10) Incubate membrane in heat-seal bag with 0.1 ml hybridization solution per cm$^2$ of membrane, 50° C. for 1–2 hours 11) Open bag, add $10^6$ cpm of probe per ml hybridization solution, and re-seal. Incubate overnight at 50° C. with gentle agitation. Temperature should be adjusted according to desired degree of stringency 12) Remove membrane from bag, soak 30 minutes in 100–200 ml 1× SSC, 0.1% SDS at room temperature with gentle agitation. Repeat.

13) Transfer membrane to 100–200 ml 0.1× SSC, 0.1% SDS, incubate 30 min at 65° C. with gentle agitation. Repeat.

14) Blot membrane dry, wrap in Saran wrap. Expose to X-ray film 1–2 days at −70° C., with intensifier screen.

| 20× SSC | Hybridization solution |
|---|---|
| 0.3 M Na Citrate, pH 7.0 | 6× SSC 1% SDS 0.1% Tween 20 |
| 3 M NaCl | 100 µg/ml yeast tRNA 50% deionized formamide |

Notes:

1) Plasmid DNA preparations should be largely free of contaminating RNA and DNA. Protocols involving the use of RNase A should be avoided. We recommend removing cellular RNA and DNA with a CsCl gradient step 2) The above protocol is recommended for transcription reactions where the concentration of the radioactive nucleotide is limiting (1–µM). This results in synthesis of full-length probes of the highest possible specific activity, at a level comparable to that obtained with the wild-type T7 promoter. If larger molar quantities of transcript (with correspondingly lower specific activities) are required, the concentration of the limiting nucleotide should be increased by adding unlabelled NTP. As the concentration of limiting nucleotide increases, however, more T7 polymerase must be added to match the yields obtained with the wild-type promoter (i.e. 20,000 units/ml required when when all 4 NTP's are at 0.5 mM).

EXAMPLE V

LITMUS 38

Description

LITMUS 38 is a multi-purpose cloning/in vitro transcription phagemid vector. The molecule is a small double-stranded circle 2814 base pairs in length (molecular weight= 1.8×10$^6$ daltons).

The key features of this vector are:

extensive set of restriction sites with unique 4-base overhangs in the polylinker blue/white selection high copy number (pUC origin)

ampicillin resistance single-stranded (M13) origin opposing T7 promoters for making RNA probes from either strand (see below)

compatible with pUC/M13 sequencing primers, as well as 4 new primers companion vector, LITMUS 39, has the same sites in opposite order.

It is preferably supplied in 10 mM Tris-HCl (pH 8.0), 1 mM EDTA.

Polylinker Region

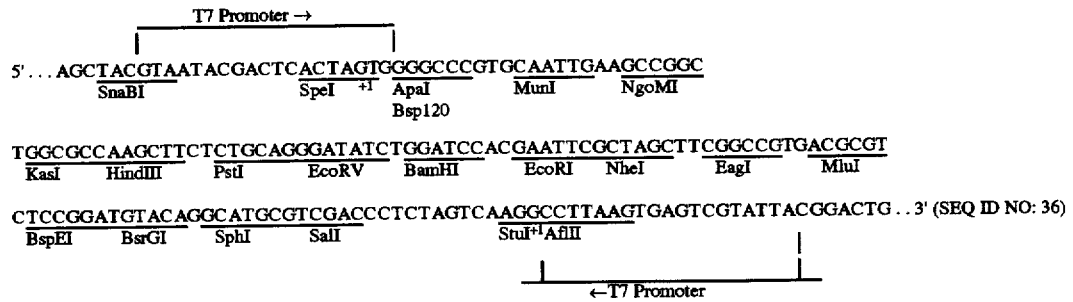

Preparation:

LITMUS 38 is isolated from *E. coli* ER2267 by a standard plasmid purification procedure.

Note: Appropriate strains of *E. coli* containing the LITMUS 38 plasmid form blue colonies on X-gal plates; when a fragment is inserted in the polylinker, the colonies are white. Blue/white selection is best achieved by plating on a rich media (e.g. LB) supplemented with X-gal (40 µg/ml) and IPTG (0.1 mM).

Production of RNA Probes from Inserts Cloned in LITMUS 38

Unlike other bidirectional transcription vectors, direction of transcription in LITMUS 38 is determined by which restriction enzyme is used to linearize the DNA template, rather than by which RNA polymerase is used. The downstream T7 promoter can be inactivated by digestion with AflII for transcription off the upstream promoter; or the upstream T7 promoter is inactivated with SpeI for transcription off the downstream promoter. If the cloned insert contains sites for either enzyme close to the active promoter, Bsp120I or StuI may be used in place of SpeI or AflII, respectively.

Protocol:

1) Digest 2–5 µg insert-containing vector with appropriate enzyme for desired direction of transcription. Purify digested DNA by phenol extraction and ethanol precipitation. Suspend in TE to 1 µg/µl. Check recovery by minigel.

2) Set up transcription reactions at room temperature as follows:

| | |
|---|---|
| 10× RNA probe buffer | 1 µl |
| 100 mM DTT | 1 µl |
| 1 mg/ml BSA | 1 µl |
| Linearized DNA, 1 µg/µl | 0.5 µl |
| α-[$^{32}$P] rNTP, 3000 Ci/mmol (CTP, ATP, or UTP) | 4 µl (40 µCi) |
| 5 mM remaining 3 NTP's | 1 µl |
| Placental RNase inhibitor, 20–40 U/µl | 0.5 µl |

| | |
|---|---|
| T7 RNA polymerase, 50 U/µl | 1 µl |
| | 10 µl |

Incubate 60–90 min at 37°–40° C.

3) Add 1 unit RNase-free DNase, incubate 15 minutes at 37° C.

4) Dilute to 200 µl with TE, add 1 µl 10 mg/ml yeast tRNA (Sigma)

5) Extract once with 200 µl 1:1 phenol:chloroform. Transfer upper layer to new tube.

6) Add 100 µl 7.5M NH$_4$OAc, 600 µl ethanol, store at −20° C. 30 min

7) Pellet RNA in microfuge 8 min, air-dry briefly, resuspend in 200 µl TE.

8) Add 50 µl 7.5M NH$_4$OAc, 500 µl ethanol and reprecipitate

9) Suspend pellet in 1 ml TE. Count 1–10 µl in scintillation counter.

Final activity should be $10^7$–$10^8$ cpm/ml. Use probe within 1–2 days.

10× RNA probe buffer 400 mM Tris-HCl, pH 7.5, 50 mM NaCl, 60 mM MgCl$_2$, 20 mM spermidine.

Membrane Hybridization with RNA Probes:

10) Incubate membrane in heat-seal bag with 0.1 ml hybridization solution per cm$^2$ of membrane, 50° C. for 1–2 hours.

11) Open bag, add $10^6$ cpm of probe per ml hybridization solution, and re-seal. Incubate overnight at 50° C. with gentle agitation. Temperature should be adjusted according to desired degree of stringency.

12) Remove membrane from bag, soak 30 minutes in 100–200 ml 1× SSC, 0.1% SDS at room temperature with gentle agitation. Repeat.

13) Transfer membrane to 100–200 ml 0.1× SSC, 0.1% SDS, incubate 30 min at 65° C. with gentle agitation. Repeat.

14) Blot membrane dry, wrap in Saran wrap. Expose to X-ray film 1–2 days at −70° C., with intensifier screen.

| 20× SSC | Hybridization solution |
|---|---|
| 0.3 M Na Citrate, pH 7.0 | 6× SSC 1% SDS |
| | 0.1% Tween 20 |
| 3 M NaCl | 100 µg/ml yeast tRNA |
| | 50% deionized formamide |

Notes:

1) Plasmid DNA preparations should be largely free of contaminating RNA and DNA. Protocols involving the use of RNase A should be avoided. We recommend removing cellular RNA and DNA with a CsCl gradient step.

2) The above protocol is recommended for transcription reactions where the concentration of the radioactive nucleotide is limiting (1–2 µM). This results in synthesis of full-length probes of the highest possible specific activity, at a level comparable to that obtained with the wild-type T7 promoter. If larger molar quantities of transcript (with correspondingly lower specific activities) are required, the concentration of the limiting nucleotide should be increased by adding unlabelled NTP. As the concentration of limiting nucleotide increases, however, more T7 polymerase must be added to match the yields obtained with the wild-type promoter (i.e. 20,000 units/ml required when when all 4 NTP's are at 0.5 mM).

What is claimed is:

1. A cloning/in vitro transcription vector comprising a vector engineered to have at least one polylinker, wherein the polylinker is flanked by opposing promoters, which promoters are recognized by a single species of RNA polymerase, and which have been modified by introduction of a first restriction endonuclease site into or proximate the first opposing promoter and a second restriction endonuclease site into or proximate the second re-opposing promoter to permit unidirectional transcription from one of the opposing promoters when the other opposing promoter has been rendered inoperable.

2. The vector of claim 1, wherein the oppossing promoters are recognized by the RNA polymerase of a bacteriophage selected from the group consisting of T7, T3, SP6, K11 and BA14.

3. The vector of claim 1, wherein the modification of the opposing promoters comprises introducing a first restriction endonuclease site into one of the opposing promoters and a second restriction endonuclease site into the other opposing promoter, whereby one or the other of the opposing promoters is rendered inoperable by the action of a restriction endonuclease which recognizes and cleaves either the first restriction site or the second restriction site but not both.

4. The vector of claim 1, wherein the modification of the opposing promoters comprises introducing a first restriction endonuclease site proximate one of the opposing promoters and a second restriction endonuclease site proximate the other opposing promoter, whereby one or the other of the opposing promoters is rendered inoperable by the action of a restriction endonuclease which recognizes and cleaves either the first restriction site or the second restriction site but not both.

5. The vector of claim 3 or 4, wherein the first and second introduced restriction sites are recognized by a Type II or Type IIS restriction endonuclease.

6. The vector of claim 5, wherein the restriction endonuclease is AflIII for the first restriction site and SpeI for the second restriction site.

7. The vector of claim 5, wherein the restriction endonuclease cleaves within the promoter.

8. The vector of claim 5, wherein the restriction endonuclease cleaves proximate the promoter.

9. The vector of claim 1, wherein the vector is a plasmid.

10. The vector of claim 1, wherein the vector is a phage.

11. The vector of claim 1, wherein the vector is a phagemid.

12. The vector of claim 11, wherein the vector is selected from the group consisting of LITMUS 28, LITMUS 29, LITMUS 38, and LITMUS 39.

13. A method for determining the tolerance of a promoter for an introduced restriction endonuclease site comprising:
    (a) introducing the restriction site within or proximal to the promoter by site-directed mutagenesis;
    (b) assaying the promoter of step (a) for transcriptional activity; and
    (c) assaying the operability of the promoter of step (b) after cleavage by a restriction endonuclease which recognizes and cleaves the restriction site.

14. The method of claim 13, wherein the restriction site is introduced into a vector containing a consensus late T7 promoter sequence.

15. The method of claim 14, wherein the vector comprises pDEFEND1.

* * * * *

UNITED STATES PATENT AND TRADEMARK OFFICE
CERTIFICATE OF CORRECTION

PATENT NO. : 5,691,140

DATED : November 25, 1997

INVENTOR(S) : Noren, et al.

It is certified that error appears in the above-identified patent and that said Letters Patent is hereby corrected as shown below:

Column 2, line 40, replace "HindIII 3:-linearized" with --*Hind*III-linearized--

Column 3, line 61, replace "pUG18" with --pUC18--.

Column 5, line 2, replace "77" with --T7--.

Column 6, line 48, replace "AflIII" with --*Afl*II--

Column 7, line 7, replace "Ase33" with --*Ase*I--

Column 7, line 10, replace "PvuIII" with --*Pvu*II--

Column 9, line 41, replace "AFl1II" with --*Afl*II--

Column 9, line 45, replace "SpeT" with --*Spe*I--

Column 10, line 30, replace "Blochem." with --*Biochem.*--

UNITED STATES PATENT AND TRADEMARK OFFICE
CERTIFICATE OF CORRECTION

PATENT NO. : 5,691,140

DATED : November 25, 1997

INVENTOR(S) : Noren, et al.

It is certified that error appears in the above-identified patent and that said Letters Patent is hereby corrected as shown below:

Column 11, line 5, replace "A(mcrC-mrr) with --Δ(*mcrC-mrr*)--

Column 11, line 5, replace "A(argF-lac) with --Δ(*argF-lac*)--

Column 11, line 21, replace "5'-pTGAGCGTGGTTCTCGC GGT-3'" with --pTGAGCGTGGTTCTCGC GGT-3;--

Column 11, line 23, replace "Cfr10T-" with --*Cfr10*I--

Column 11, last line, replace "GACIA" with --GACCTA--.

Column 14, line 56, replace "TCCGGA" with --TCCGGAC--

Column 17, line 65, replace "10" with --10--

Column 18, line 42, replace "(1-μM)" with --(1-2 μM)--

UNITED STATES PATENT AND TRADEMARK OFFICE
CERTIFICATE OF CORRECTION

PATENT NO. : 5,691,140

DATED : November 25, 1997

INVENTOR(S) : Noren, et al.

It is certified that error appears in the above-identified patent and that said Letters Patent is hereby corrected as shown below:

Column 19, line 16, replace "$^{+1}$ Apa I" with --$^{+1}$Apa I--

Column 19, line 18, replace "AGGGATATC" with --AGGATATC--

Column 19, line 62, replace "0.5 μ" with --0.5 μl--

Column 20, line 64, replace "3 M NaCI" with --3 M NACl--.

Signed and Sealed this

Seventh Day of April, 1998

Attest:

Attesting Officer

BRUCE LEHMAN

Commissioner of Patents and Trademarks

UNITED STATES PATENT AND TRADEMARK OFFICE
CERTIFICATE OF CORRECTION

Page 1 of 3

PATENT NO. : 5,691,140
DATED : November 25, 1997
INVENTOR(S) : Noren, et. al.

It is certified that error appears in the above-indentified patent and that said Letters Patent is hereby corrected as shown below:

Sheet 2 of 11, replace "AflII" with --AfI I I--

Sheet 3 of 11, replace "AflII" with --AfI I I--

Sheet 4 of 11, replace "v [template]" with --v/[template]--

Sheet 6 of 11, Column Under 28, 3rd line, relace "NsI" with --N s i--

Sheet 6 of 11, Column Under 28, 5th line, relace "BsI" with --B s i--

Sheet 6 of 11, Column Under 29, 15th line, replace "BsI" with --B s i--

Sheet 6 of 11, Column Under 29, 17th line, replace "NsI" with --N s i--

Sheet 8 of 11, line 15, replace "MfeI" with --Mun I--

UNITED STATES PATENT AND TRADEMARK OFFICE
CERTIFICATE OF CORRECTION

PATENT NO. : 5,691,140
DATED : November 25, 1997
INVENTOR(S) : Noren, et. al.

It is certified that error appears in the above-indentified patent and that said Letters Patent is hereby corrected as shown below:

Sheet 8 of 11, line 24, replace "Mfel" with -- MunI--

Column 2, line 63, replace "based" with --base--

Column 3, line 15, replace "gray bars" with
--right to left diagonal lines--

Column 3, line 15, replace "striped bars" with
--left to right diagonal lines--

Column 4, line 60, replace "restiction" with --restriction--

Column 7, line 29, replace          with --AatII--

Column 10, line 46, replace "Example" with --Examples--

Column 11, line 2, replace "thii" with --thi-1--

UNITED STATES PATENT AND TRADEMARK OFFICE
CERTIFICATE OF CORRECTION

PATENT NO. : 5,691,140
DATED : November 25, 1997
INVENTOR(S) : Noren, et. al.

It is certified that error appears in the above-indentified patent and that said Letters Patent is hereby corrected as shown below:

Column 12, line 50, replace "LITMUS 28" with --LITMUS 38--

Signed and Sealed this

Thirtieth Day of June, 1998

Attest:

BRUCE LEHMAN

*Attesting Officer*  *Commissioner of Patents and Trademarks*

SEQUENCE LISTING ( 1 ) GENERAL INFORMATION:

( i i i ) NUMBER OF SEQUENCES: 36

( 2 ) INFORMATION FOR SEQ ID NO:1:

( i ) SEQUENCE CHARACTERISTICS:
      ( A ) LENGTH: 183 base pairs
      ( B ) TYPE: nucleic acid
      ( C ) STRANDEDNESS: single
      ( D ) TOPOLOGY: unknown ( i i ) MOLECULE TYPE: DNA (genomic)

( x i ) SEQUENCE DESCRIPTION: SEQ ID NO:1:

```
AGCTACGTAA  TACGACTCAC  TAGTGGGCAG  ATCTTCGAAT  GCATCGCGCG  CACCGTACGT      60
CTCGAGGAAT  TCCTGCAGGA  TATCTGGATC  CACGAAGCTT  CCCATGGTGA  CGTCACCGGT     120
TCTAGATACC  TAGGTGAGCT  CTGGTACCCT  CTAGTCAAGG  CCTTAAGTGA  GTCGTATTAC     180
GGA                                                                        183
```

( 2 ) INFORMATION FOR SEQ ID NO:2:

( i ) SEQUENCE CHARACTERISTICS:
      ( A ) LENGTH: 180 base pairs
      ( B ) TYPE: nucleic acid
      ( C ) STRANDEDNESS: single
      ( D ) TOPOLOGY: unknown ( i i ) MOLECULE TYPE: DNA (genomic)

( x i ) SEQUENCE DESCRIPTION: SEQ ID NO:2:

```
AGCTACGTAA  TACGACTCAC  TAGTGGGTAC  CAGAGCTCCC  TAGGTTCTAG  AACCGGTGAC      60
GTCTCCCATG  GTGAAGCTTG  GATCCACGAT  ATCCTGCAGG  AATTCCTCGA  GACCGTACGT     120
GCGCGCGAAT  GCATCCAGAT  CTTCCCTCTA  GTCAAGGCCT  TAAGTGAGTC  GTATTACGGA     180
```

( 2 ) INFORMATION FOR SEQ ID NO:3:

( i ) SEQUENCE CHARACTERISTICS:
      ( A ) LENGTH: 174 base pairs
      ( B ) TYPE: nucleic acid
      ( C ) STRANDEDNESS: single
      ( D ) TOPOLOGY: unknown ( i i ) MOLECULE TYPE: DNA (genomic)

( x i ) SEQUENCE DESCRIPTION: SEQ ID NO:3:

```
AGCTACGTAA  TACGACTCAC  TAGTGGGGCC  CGTGCAATTG  AAGCCGGCTG  GCGCCAAGCT      60
TCTCTGCAGG  ATATCTGGAT  CCACGAATTC  GCTAGCTTCG  GCCGTGACGC  GTCTCCGGAT     120
GTACAGGCAT  GCGTCGACCC  TCTAGTCAAG  GCCTTAAGTG  AGTCGTATTA  CGGA           174
```

( 2 ) INFORMATION FOR SEQ ID NO:4:

( i ) SEQUENCE CHARACTERISTICS:
   ( A ) LENGTH: 180 base pairs
   ( B ) TYPE: nucleic acid
   ( C ) STRANDEDNESS: single
   ( D ) TOPOLOGY: unknown ( i i ) MOLECULE TYPE: DNA (genomic)

( x i ) SEQUENCE DESCRIPTION: SEQ ID NO:4:

| | | | | | |
|---|---|---|---|---|---|
| AGCTACGTAA | TACGACTCAC | TAGTGGGTCG | ACCGCATGCC | TGTACACTCC | GGAAGACGCG | 60
| TTCGGCCGTG | CTAGCGAATT | CTGGATCCAC | GATATCCTGC | AGGAAGCTTT | CTGGCGCCTG | 120
| GCCGGCGCAA | TTGAATGGGC | CCCTCTAGTC | AAGGCCTTAA | GTGAGTCGTA | TTACGGACTG | 180

( 2 ) INFORMATION FOR SEQ ID NO:5:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: unknown ( i i ) MOLECULE TYPE: DNA (genomic)

( x i ) SEQUENCE DESCRIPTION: SEQ ID NO:5:

TAATACGACT CACTATAG                    18

( 2 ) INFORMATION FOR SEQ ID NO:6:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: unknown ( i i ) MOLECULE TYPE: DNA (genomic)

( x i ) SEQUENCE DESCRIPTION: SEQ ID NO:6:

TAATACGACT CACTATAGGG                   20

( 2 ) INFORMATION FOR SEQ ID NO:7:

( i ) SEQUENCE CHARACTERISTICS:
      ( A ) LENGTH: 6 base pairs
      ( B ) TYPE: nucleic acid
      ( C ) STRANDEDNESS: single
      ( D ) TOPOLOGY: unknown ( i i ) MOLECULE TYPE: DNA (genomic)

( x i ) SEQUENCE DESCRIPTION: SEQ ID NO:7:

CTTAAG                                  6

( 2 ) INFORMATION FOR SEQ ID NO:8:

( i ) SEQUENCE CHARACTERISTICS:
      ( A ) LENGTH: 6 base pairs
      ( B ) TYPE: nucleic acid
      ( C ) STRANDEDNESS: single
      ( D ) TOPOLOGY: unknown ( i i ) MOLECULE TYPE: DNA (genomic)

( x i ) SEQUENCE DESCRIPTION: SEQ ID NO:8:

CTCGAG                                  6

( 2 ) INFORMATION FOR SEQ ID NO:9:

( i ) SEQUENCE CHARACTERISTICS:
    ( A ) LENGTH: 6 base pairs
    ( B ) TYPE: nucleic acid
    ( C ) STRANDEDNESS: single
    ( D ) TOPOLOGY: unknown ( i i ) MOLECULE TYPE: DNA (genomic)

( x i ) SEQUENCE DESCRIPTION: SEQ ID NO:9:

CAATTG      6

( 2 ) INFORMATION FOR SEQ ID NO:10:

( i ) SEQUENCE CHARACTERISTICS:
    ( A ) LENGTH: 6 base pairs
    ( B ) TYPE: nucleic acid
    ( C ) STRANDEDNESS: single
    ( D ) TOPOLOGY: unknown ( i i ) MOLECULE TYPE: DNA (genomic)

( x i ) SEQUENCE DESCRIPTION: SEQ ID NO:10:

CCATGG      6

( 2 ) INFORMATION FOR SEQ ID NO:11:

( i ) SEQUENCE CHARACTERISTICS:
    ( A ) LENGTH: 6 base pairs
    ( B ) TYPE: nucleic acid
    ( C ) STRANDEDNESS: single
    ( D ) TOPOLOGY: unknown ( i i ) MOLECULE TYPE: DNA (genomic)

( x i ) SEQUENCE DESCRIPTION: SEQ ID NO:11:

CATATG      6

( 2 ) INFORMATION FOR SEQ ID NO:12:

( i ) SEQUENCE CHARACTERISTICS:
    ( A ) LENGTH: 6 base pairs
    ( B ) TYPE: nucleic acid
    ( C ) STRANDEDNESS: single
    ( D ) TOPOLOGY: unknown ( i i ) MOLECULE TYPE: DNA (genomic)

( x i ) SEQUENCE DESCRIPTION: SEQ ID NO:12:

TCTAGA      6

( 2 ) INFORMATION FOR SEQ ID NO:13:

( i ) SEQUENCE CHARACTERISTICS:
    ( A ) LENGTH: 6 base pairs
    ( B ) TYPE: nucleic acid
    ( C ) STRANDEDNESS: single
    ( D ) TOPOLOGY: unknown ( i i ) MOLECULE TYPE: DNA (genomic)

( x i ) SEQUENCE DESCRIPTION: SEQ ID NO:13:

ACTAGT      6

( 2 ) INFORMATION FOR SEQ ID NO:14:

( i ) SEQUENCE CHARACTERISTICS:
    ( A ) LENGTH: 11 base pairs
    ( B ) TYPE: nucleic acid
    ( C ) STRANDEDNESS: single
    ( D ) TOPOLOGY: unknown ( i i ) MOLECULE TYPE: DNA (genomic)

( x i ) SEQUENCE DESCRIPTION: SEQ ID NO:14:

CCTACTATAG G          11

( 2 ) INFORMATION FOR SEQ ID NO:15:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:15:

GGCGAATGGC GCTTCGCTTG GTAATAAAAG CCCGCTTCGG CGGGCTTTTT TTTGTTAACT          60

ACGTCAGGT          69

( 2 ) INFORMATION FOR SEQ ID NO:16:

( i ) SEQUENCE CHARACTERISTICS:
        ( A ) LENGTH: 7 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:16:

Gly Glu Trp Arg Phe Ala Trp
1                 5

( 2 ) INFORMATION FOR SEQ ID NO:17:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:17:

TGAGCGTGGT TCTCGCGGT          19

( 2 ) INFORMATION FOR SEQ ID NO:18:

( i ) SEQUENCE CHARACTERISTICS:
        ( A ) LENGTH: 83 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:18:

AATTATAATA CGACTCACTA TAGGGAGACC GAATTCGCAA GCTTGCGTCA TCCTATTCTA          60

TAGTGTCACC TAAATCGTAT GGT          83

( 2 ) INFORMATION FOR SEQ ID NO:19:

( i ) SEQUENCE CHARACTERISTICS:
        ( A ) LENGTH: 83 base pairs
        ( B ) TYPE: nucleic acid
        ( C ) STRANDEDNESS: single
        ( D ) TOPOLOGY: unknown (ii) MOLECULE TYPE: DNA (genomic)

(xi) SEQUENCE DESCRIPTION: SEQ ID NO:19:

ATAATACGAC TCACTATAGG GAGACCGAAT TCGCAAGCTT GCGTCATCCT ATTCTATAGT    60

GTCACCTAAA TCGTATGTTA GCT    83

(2) INFORMATION FOR SEQ ID NO:20:

(i) SEQUENCE CHARACTERISTICS:
        (A) LENGTH: 22 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:20:

ACGACTCACT TAAGGGAGAC CG    22

(2) INFORMATION FOR SEQ ID NO:21:

(i) SEQUENCE CHARACTERISTICS:
        (A) LENGTH: 22 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:21:

ACGACTCACT CGAGGGAGAC CG    22

(2) INFORMATION FOR SEQ ID NO:22:

(i) SEQUENCE CHARACTERISTICS:
        (A) LENGTH: 24 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:22:

TACGACTCAC AATTGGGAGA CCGA    24

(2) INFORMATION FOR SEQ ID NO:23:

(i) SEQUENCE CHARACTERISTICS:
        (A) LENGTH: 24 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:23:

TACGACTCAC CATGGGGAGA CCGA    24

(2) INFORMATION FOR SEQ ID NO:24:

(i) SEQUENCE CHARACTERISTICS:
        (A) LENGTH: 30 base pairs
        (B) TYPE: nucleic acid
        (C) STRANDEDNESS: single
        (D) TOPOLOGY: unknown (ii) MOLECULE TYPE: DNA (genomic)

( x i ) SEQUENCE DESCRIPTION: SEQ ID NO:24:

TAATACGACT CACATATGGG AGACCGAATT                                                         30

( 2 ) INFORMATION FOR SEQ ID NO:25:

( i ) SEQUENCE CHARACTERISTICS:
          ( A ) LENGTH: 25 base pairs
          ( B ) TYPE: nucleic acid
          ( C ) STRANDEDNESS: single
          ( D ) TOPOLOGY: unknown ( i i ) MOLECULE TYPE: DNA (genomic)

( x i ) SEQUENCE DESCRIPTION: SEQ ID NO:25:

AATACGACTC TCTAGAGGGA GACCG                                                              25

( 2 ) INFORMATION FOR SEQ ID NO:26:

( i ) SEQUENCE CHARACTERISTICS:
          ( A ) LENGTH: 22 base pairs
          ( B ) TYPE: nucleic acid
          ( C ) STRANDEDNESS: single
          ( D ) TOPOLOGY: unknown ( i i ) MOLECULE TYPE: DNA (genomic)

( x i ) SEQUENCE DESCRIPTION: SEQ ID NO:26:

CGACTCACTA GTGGGAGACC GA                                                                 22

( 2 ) INFORMATION FOR SEQ ID NO:27:

( i ) SEQUENCE CHARACTERISTICS:
          ( A ) LENGTH: 28 base pairs
          ( B ) TYPE: nucleic acid
          ( C ) STRANDEDNESS: single
          ( D ) TOPOLOGY: unknown ( i i ) MOLECULE TYPE: DNA (genomic)

( x i ) SEQUENCE DESCRIPTION: SEQ ID NO:27:

GAATTATAAT ACGACCTACT ATAAGGAG                                                           28

( 2 ) INFORMATION FOR SEQ ID NO:28:

( i ) SEQUENCE CHARACTERISTICS:
          ( A ) LENGTH: 55 base pairs
          ( B ) TYPE: nucleic acid
          ( C ) STRANDEDNESS: single
          ( D ) TOPOLOGY: unknown ( i i ) MOLECULE TYPE: DNA (genomic)

( x i ) SEQUENCE DESCRIPTION: SEQ ID NO:28:

GCGCTTCGCT TGGTAATAAA GCCCGCTTCG GCGGGCTTTT TTTTGTTAAC TACGT                              55

( 2 ) INFORMATION FOR SEQ ID NO:29:

( i ) SEQUENCE CHARACTERISTICS:
          ( A ) LENGTH: 47 base pairs
          ( B ) TYPE: nucleic acid
          ( C ) STRANDEDNESS: single
          ( D ) TOPOLOGY: unknown ( i i ) MOLECULE TYPE: DNA (genomic)

( x i ) SEQUENCE DESCRIPTION: SEQ ID NO:29:

TTCGCTTGGT AATAAAGCCC GCTTCGGCGG GCTTTTTTTT GTTAACT                                      47

( 2 ) INFORMATION FOR SEQ ID NO:30:

( i ) SEQUENCE CHARACTERISTICS:
        ( A ) LENGTH: 99 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:30:

```
AGCTGGGCCC GTGCAATTGA AGCCGGCTGG CGCCAAGCTT CTCTGCAGGA TATCTGGATC     60
CACGAATTCG CTAGCTTCGG CCGTGACGCG TCTCCGGAC                            99
```

( 2 ) INFORMATION FOR SEQ ID NO:31:

( i ) SEQUENCE CHARACTERISTICS:
        ( A ) LENGTH: 99 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:31:

```
GGGCCCGTGC AATTGAAGCC GGCTGGCGCC AAGCTTCTCT GCAGGATATC TGGATCCACG     60
AATTCGCTAG CTTCGGCCGT GACGCGTCTC CGGACAATT                            99
```

( 2 ) INFORMATION FOR SEQ ID NO:32:

( i ) SEQUENCE CHARACTERISTICS:
        ( A ) LENGTH: 94 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:32:

```
AGCTACGTAA TACGACTCAC TAGTGGGGCC CGTTAATCCG GATGTACAGG CATGCGTCGA     60
CCCTCTAGTC AAGGCCTTAA GTGAGTCGTA TTAT                                 94
```

( 2 ) INFORMATION FOR SEQ ID NO:33:

( i ) SEQUENCE CHARACTERISTICS:
        ( A ) LENGTH: 94 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:33:

```
ACGTAATACG ACTCACTAGT GGGGCCCGTT AATCCGGATG TACAGGCATG CGTCGACCCT     60
CTAGTCAAGG CCTTAAGTGA GTCGTATTAT AATT                                 94
```

( 2 ) INFORMATION FOR SEQ ID NO:34:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:34:

```
GGCCTTAAGT  GAGTCGTATT  ACGGACTGGC  CGTCGTTTTA  CAACG                    45
```

( 2 ) INFORMATION FOR SEQ ID NO:35:

( i ) SEQUENCE CHARACTERISTICS:
        ( A ) LENGTH: 180 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:35:

```
AGCTACGTAA  TACGACTCAC  TAGTGGGCAG  ATCTTCGAAT  GCATCGCGCG  CACCGTACGT    60

CTCGAGGAAT  TCCTGCAGGA  TATCTGGATC  CACGAAGCTT  CCCATGGTGA  CGTCACCGGT   120

TCTAGATACC  TAGGTGAGCT  CTGGTACCCT  CTAGTCAAGG  CCTTAAGTGA  GTCGTATTAC   180
```

( 2 ) INFORMATION FOR SEQ ID NO:36:

( i ) SEQUENCE CHARACTERISTICS:
        ( A ) LENGTH: 177 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:36:

```
AGCTACGTAA  TACGACTCAC  TAGTGGGGCC  CGTGCAATTG  AAGCCGGCTG  GCGCCAAGCT    60

TCTCTGCAGG  ATATCTGGAT  CCACGAATTC  GCTAGCTTCG  GCCGTGACGC  GTCTCCGGAT   120

GTACAGGCAT  GCGTCGACCC  TCTAGTCAAG  GCCTTAAGTG  AGTCGTATTA  CGGACTG     177
```